US010323102B2

(12) United States Patent
Dennes et al.

(10) Patent No.: US 10,323,102 B2
(45) Date of Patent: *Jun. 18, 2019

(54) CATIONIC POLY ALPHA-1,3-GLUCAN ETHERS

(71) Applicant: E I DU PONT DE NEMOURS AND COMPANY, Wilmington, DE (US)

(72) Inventors: T. Joseph Dennes, Parkesburg, PA (US); Andrea M. Perticone, Clayton, DE (US); Jayme L. Paullin, Claymont, DE (US)

(73) Assignee: E I DU PONT DE NEMOURS AND COMPANY, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/945,819

(22) Filed: Apr. 5, 2018

(65) Prior Publication Data

US 2018/0223002 A1  Aug. 9, 2018

Related U.S. Application Data

(63) Continuation of application No. 15/103,682, filed as application No. PCT/US2014/070906 on Dec. 17, 2014, now Pat. No. 9,957,334.

(60) Provisional application No. 61/917,507, filed on Dec. 18, 2013, provisional application No. 62/014,273, filed on Jun. 19, 2014.

(51) Int. Cl.
*C08L 5/00* (2006.01)
*C08B 37/00* (2006.01)
*A61K 8/73* (2006.01)
*A61Q 11/00* (2006.01)
*C11D 3/22* (2006.01)
*C11D 17/00* (2006.01)

(52) U.S. Cl.
CPC ............ *C08B 37/0009* (2013.01); *A61K 8/73* (2013.01); *A61Q 11/00* (2013.01); *C08L 5/00* (2013.01); *C11D 3/227* (2013.01); *C11D 17/003* (2013.01); *C11D 17/0008* (2013.01); *A61K 2800/48* (2013.01); *A61K 2800/5426* (2013.01)

(58) Field of Classification Search
CPC ........ C11D 1/662; C11D 3/227; A61K 8/731; C08B 37/0009; C08L 5/00
See application file for complete search history.

(56) References Cited

U.S. PATENT DOCUMENTS

| 4,580,421 | A | 4/1986 | Babuin et al. |
|---|---|---|---|
| 4,794,661 | A | 1/1989 | Durazzani |
| 5,558,861 | A | 9/1996 | Yamanaka et al. |
| 5,945,394 | A | 8/1999 | Sajic et al. |
| 5,952,205 | A | 9/1999 | Catani et al. |
| 6,045,780 | A | 4/2000 | Bixler et al. |
| 6,242,225 | B1 | 6/2001 | Catani et al. |
| 6,342,486 | B1 | 1/2002 | Zulli et al. |
| 6,579,840 | B1 | 6/2003 | Heltovics |
| 6,660,502 | B2 | 12/2003 | Catani et al. |
| 6,730,646 | B1 | 5/2004 | Waschenbach et al. |
| 7,000,000 | B1 | 2/2006 | O'Brien |
| 7,001,878 | B2 | 2/2006 | De Buzzaccarini et al. |
| 7,012,053 | B1 | 3/2006 | Barnabas et al. |
| 7,056,880 | B2 | 6/2006 | Wang et al. |
| 7,534,759 | B2 | 5/2009 | Wahl et al. |
| 7,576,048 | B2 | 8/2009 | Gray et al. |
| 8,076,299 | B2 | 12/2011 | Brand et al. |
| 9,351,910 | B2 | 5/2016 | Chen et al. |
| 9,714,403 | B2 * | 7/2017 | Nagy .................. A61K 8/66 |
| 9,771,548 | B2 | 9/2017 | Nagy et al. |
| 9,957,334 | B2 * | 5/2018 | Dennes ............. C08B 37/0009 |
| 10,190,079 | B2 * | 1/2019 | Nagy .................. A61K 8/66 |
| 2002/0022006 | A1 | 2/2002 | Jung |
| 2004/0151681 | A1 | 8/2004 | Busk et al. |
| 2005/0059633 | A1 | 3/2005 | Van Geel-Schuten |
| 2006/0134025 | A1 | 6/2006 | Trivedi et al. |
| 2006/0134417 | A1 | 6/2006 | Takaha et al. |
| 2008/0057007 | A1 | 3/2008 | Leonhardt et al. |
| 2009/0209445 | A1 | 8/2009 | Panandiker et al. |
| 2010/0081598 | A1 | 4/2010 | Sharma et al. |
| 2012/0168698 | A1 | 7/2012 | Hammond |
| 2013/0236630 | A1 | 9/2013 | Brizius |
| 2013/0244288 | A1 | 9/2013 | O'Brien et al. |

(Continued)

FOREIGN PATENT DOCUMENTS

| CN | 1283633 A | 2/2001 |
|---|---|---|
| EP | 0035478 A1 | 9/1981 |

(Continued)

OTHER PUBLICATIONS

Wang et al, "Synthesis of quaternary (1-3)-alpha-D-glucan and its antibacterial activity", Journal of Beijing University of Chemical Technology (Natural Science Edition), 34(4), pp. 418-420, 2007.*
Wang et al., 2007, Synthesis of Quaternary (1-3)-Alpha-D-Glucan and Its Antibacterial Activity, Journal of Beijing University of Chemical Technology (Natural Science Edition), 34(4):418-420.
Joucla et al., Construction of a Fully Active Truncated Alternansucrase Partially Deleted of Its Carboxy-Tmerinal Domain, FEBS Letters, vol. 580 (2006), pp. 763-768.

(Continued)

*Primary Examiner* — Brian P Mruk

(57) ABSTRACT

Poly alpha-1,3-glucan ether compounds are disclosed herein comprising positively charged organic groups. The degree of substitution of the ether compounds is about 0.05 to about 3.0. Also disclosed are methods of producing poly alpha-1, 3-glucan ether compounds having positively charged organic groups, as well as methods of using these ether compounds for increasing the viscosity of a aqueous compositions. Hydrocolloids and aqueous solutions comprising the ether compounds are also disclosed.

67 Claims, No Drawings

(56) References Cited

U.S. PATENT DOCUMENTS

| | | |
|---|---|---|
| 2014/0087431 A1 | 3/2014 | Payne et al. |
| 2014/0179913 A1 | 6/2014 | Paullin et al. |
| 2015/0080220 A1 | 3/2015 | Yao et al. |
| 2015/0232785 A1 | 8/2015 | Paullin et al. |
| 2015/0368594 A1 | 12/2015 | Nagy et al. |
| 2015/0368595 A1 | 12/2015 | Nagy et al. |

FOREIGN PATENT DOCUMENTS

| | | |
|---|---|---|
| EP | 0819703 A2 | 1/1998 |
| GB | 2095275 A | 9/1982 |
| GB | 2432852 A | 6/2007 |
| JP | 2000159806 A | 6/2000 |
| JP | 2013091771 | 5/2013 |
| WO | 2013026182 A1 | 2/2013 |
| WO | 2013036968 A1 | 3/2013 |
| WO | 2013068771 A1 | 5/2013 |
| WO | 2013158992 A1 | 10/2013 |
| WO | 2014099724 A1 | 6/2014 |
| WO | 2015095046 A1 | 6/2015 |

OTHER PUBLICATIONS

Yathindra, et al., Configurational Statistics of Polysaccharides, Current Science, vol. 42, No. 23 (1973), pp. 809-811.

Yui et al., Molecular and Crystal Structure of (1->3)-α-D-Glucan Triacetate, Int. J. Macromol., vol. 14 (1992), pp. 87-96.

Abo et al., Peptide Sequences for Sucrose Splitting and Glucan Binding Within *Streptococcus sobrinus* Glucosyltransferase (Water-Insoluble Glucan Synthetase), Journal of Bacteriology, vol. 173, No. 3 (1991), pp. 989-996.

Bao et al., Chemical Modifications of the (1->3)-α-D-Glucan From Spores of Ganoderma Lucidum and Investigation of Their Physicochemical Properties and Immunological Activity, Carbohydrate Research, vol. 336 (2001), pp. 127-140.

Cantarel et al., The Carbohydrate-Active Enzymes Database (CAZY): An Expert Resource for Glycogenomics, Nucleic Acids Research, vol. 37 (2009), Database Issue, pp. D-233-D238.

Jeanes et al., Characterization and Classification of Dextrans From Ninety-Six Strains Bacteria, Contributino From the Starch and Dextrose Section, Northern Utilization of Research Branch, vol. 76 (1954), pp. 5041-5052.

Simpson et al., Four Glucosyltransferases, GTFJ, GTFK, GTFL and GTFM, From *Streptococcus salivarius* ATCC 25975, Microbiology, vol. 141 (1995), pp. 1451-1460.

Kiho et al., (1->3)-α-D-Glucan From an Alkaline Extract of Agrocybe Cylindracea and Antitumor Activity of Its O-(Carboxy-Methyl)ated Derivatives, Carbohydrate Research, vol. 189 (1989), pp. 273-279.

Konishi et al., Structure and Enzymatic Properties of Genetically Truncated Forms of the Water-Insoluble Glucan-Synthesizing Glucosyltransferase From *Streptococcus sobrinus*, J. Biochem, vol. 126 (1999), pp. 287-295.

Monchois et al., Isolation of an Active Catalytic Core of *Streptococcus downei* MFE28 GTF-I Glucosyltranserase, Journal of Bacteriology, vol. 181, No. 7 (1999), pp. 2290-2292.

Monchois et al., Glucansucrases: Mechanism of Action and Structure-Function Relationships, FEMS Microbiology Review, vol. 23 (1999), pp. 131-151.

Ogawa et al., X-Ray Diffraction Data for (1->3)-α-D-Glucan Triacetate, Carbohydrate Polymers, vol. 3 (1983), pp. 287-297.

Ogawa et al., Crystal Structure of (1->3)-α-D-Glucan, in Fiber Defraction Methods, French, A. et al., ACS Symposium Series: American Chemical Society, Washington, DC (1980), pp. 353-362.

Shida et al., A (1->3)-α-D-Glucan Isolated From the Fruit Bodies of Lentinus Edodes, Carbohydrate Research, vol. 60 )1978), pp. 117-127.

International Search Report, PCT Application No. PCT/US2014/070906, dated May 27, 2015.

\* cited by examiner

CATIONIC POLY ALPHA-1,3-GLUCAN ETHERS

This application is a continuation of application Ser. No. 15/103,682 (filed Jun. 10, 2016) (now U.S. Pat. No. 9,957,334), which is a National Stage application of International Application No. PCT/US2014/070906 (filed Dec. 17, 2014), which claims the benefit of U.S. Provisional Application Nos. 61/917,507 (filed Dec. 18, 2013) and 62/014,273 (filed Jun. 19, 2014). All of these prior applications are incorporated herein by reference in their entireties.

FIELD OF INVENTION

This invention is in the field of poly alpha-1,3-glucan derivatives. Specifically, this invention pertains to cationic poly alpha-1,3-glucan ethers and methods of their preparation and use as viscosity modifiers.

BACKGROUND

Driven by a desire to find new structural polysaccharides using enzymatic syntheses or genetic engineering of microorganisms or plant hosts, researchers have discovered polysaccharides that are biodegradable, and that can be made economically from renewable resource-based feedstocks. One such polysaccharide is poly alpha-1,3-glucan, a glucan polymer characterized by having alpha-1,3-glycosidic linkages. This polymer has been isolated by contacting an aqueous solution of sucrose with a glucosyltransferase enzyme isolated from *Streptococcus salivarius* (Simpson et al., *Microbiology* 141:1451-1460, 1995).

U.S. Pat. No. 7,000,000 disclosed the preparation of a polysaccharide fiber comprising hexose units, wherein at least 50% of the hexose units within the polymer were linked via alpha-1,3-glycosidic linkages using an *S. salivarius* gtfJ enzyme. This enzyme utilizes sucrose as a substrate in a polymerization reaction producing poly alpha-1,3-glucan and fructose as end-products (Simpson et al., 1995). The disclosed polymer formed a liquid crystalline solution when it was dissolved above a critical concentration in a solvent or in a mixture comprising a solvent. From this solution continuous, strong, cotton-like fibers, highly suitable for use in textiles, were spun and used.

Kiho et al. (*Carb. Res.* 189:273-270, 1989) disclosed the alkaline extraction and isolation of poly alpha-1,3-glucan from the fungus, Agrocybe cylindracea, which was further derivatized to sodium carboxymethylglucan (CMG). This ether derivative exhibited anti-tumor properties against sarcoma. Similarly, Zhang et al. (Intl. Publ. No. CN1283633) described the extraction of poly alpha-1,3-glucan from the medicinal fungus, *Ganoderma lucidum*, and its derivatization to CMG.

SUMMARY OF INVENTION

In one embodiment, the invention concerns a composition comprising a poly alpha-1,3-glucan ether compound represented by the structure:

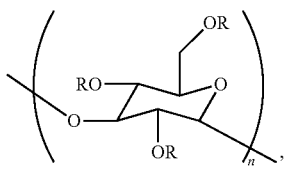

wherein (i) n is at least 6, (ii) each R is independently an H or a positively charged organic group, and (iii) the compound has a degree of substitution of about 0.05 to about 3.0.

In a second embodiment, at least one positively charged organic group comprises a substituted ammonium group. This positively charged organic group can comprise a trimethylammonium group in a third embodiment. In a fourth embodiment, the positively charged organic group can be a quaternary ammonium group.

In a fifth embodiment, at least one positively charged organic group comprises an alkyl group or hydroxy alkyl group. The compound in this embodiment may contain one type of positively charged organic group, or two or more types of positively charged organic group. At least one positively charged organic group can be a quaternary ammonium hydroxypropyl group, for example.

In a sixth embodiment, the invention concerns a method for producing a poly alpha-1,3-glucan ether compound. This method comprises contacting poly alpha-1,3-glucan in a reaction under alkaline conditions with at least one etherification agent comprising a positively charged organic group. At least one positively charged organic group is etherified to the poly alpha-1,3-glucan in this contacting step, thereby producing a poly alpha-1,3-glucan ether compound represented by the structure:

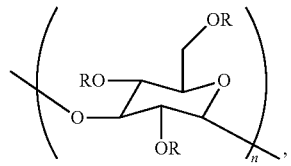

wherein (i) n is at least 6, (ii) each R is independently an H or the positively charged organic group, and (iii) the compound has a degree of substitution of about 0.05 to about 3.0. A poly alpha-1,3-glucan ether compound produced by this method can optionally be isolated.

In a seventh embodiment, the alkaline conditions of the reaction comprise an alkali hydroxide solution.

In an eighth embodiment, the reaction comprises an organic solvent. The organic solvent is isopropanol in a ninth embodiment.

In a tenth embodiment, the contacting step of the method further comprises heating the reaction, and/or neutralizing the pH of the reaction.

In an eleventh embodiment of the method, at least one positively charged organic group comprises a substituted ammonium group. At least one positively charged organic group comprises a trimethylammonium group in a twelfth embodiment.

In a thirteenth embodiment, the invention concerns a hydrocolloid or aqueous solution comprising a poly alpha-1,3-glucan ether compound represented by the structure:

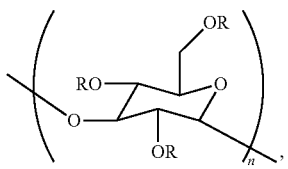

wherein
(i) n is at least 6,
(ii) each R is independently an H or a positively charged organic group,
(iii) the compound has a degree of substitution of about 0.05 to about 3.0, and
(iv) the hydrocolloid or aqueous solution has a viscosity of at least about 10 cPs.

In a fourteenth embodiment, the invention concerns a method for increasing the viscosity of an aqueous composition. This method comprises contacting a poly alpha-1,3-glucan ether compound as disclosed herein with an aqueous composition, thereby increasing the viscosity of the aqueous composition.

In a fifteenth embodiment, the invention concerns a method of treating a material. This method comprises contacting a material with an aqueous composition comprising a poly alpha-1,3-glucan ether compound as disclosed herein. The poly alpha-1,3-glucan ether compound adsorbs to the surface of the material in certain embodiments of this method.

DETAILED DESCRIPTION OF INVENTION

The disclosures of all patent and non-patent literature cited herein are incorporated herein by reference in their entirety.

As used herein, the term "invention" or "disclosed invention" is not meant to be limiting, but applies generally to any of the inventions defined in the claims or described herein. These terms are used interchangeably herein.

The terms "poly alpha-1,3-glucan", "alpha-1,3-glucan polymer" and "glucan polymer" are used interchangeably herein. Poly alpha-1,3-glucan is a polymer comprising glucose monomeric units linked together by glycosidic linkages (i.e., glucosidic linkages), wherein at least about 50% of the glycosidic linkages are alpha-1,3-glycosidic linkages. Poly alpha-1,3-glucan is a type of polysaccharide. The structure of poly alpha-1,3-glucan can be illustrated as follows:

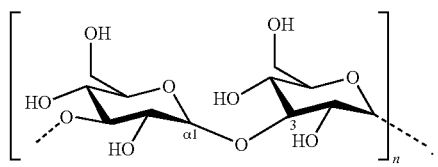

Poly alpha-1,3-glucan that can be used for preparing poly alpha-1,3-glucan ether compounds herein can be prepared using chemical methods. Alternatively, it can be prepared by extracting it from various organisms, such as fungi, that produce poly alpha-1,3-glucan. Alternatively still, poly alpha-1,3-glucan can be enzymatically produced from sucrose using one or more glucosyltransferase (gtf) enzymes (e.g., gtfJ), such as described in U.S. Pat. No. 7,000,000, and U.S. Patent Appl. Publ. Nos. 2013/0244288 and 2013/0244287 (all of which are incorporated herein by reference), for example.

The terms "glucosyltransferase enzyme", "gtf enzyme", "gtf enzyme catalyst", "gtf", and "glucansucrase" are used interchangeably herein. The activity of a gtf enzyme herein catalyzes the reaction of the substrate sucrose to make the products poly alpha-1,3-glucan and fructose. Other products (byproducts) of a gtf reaction can include glucose (results from when glucose is hydrolyzed from the glucosyl-gtf enzyme intermediate complex), various soluble oligosaccharides (e.g., DP2-DP7), and leucrose (results from when glucose of the glucosyl-gtf enzyme intermediate complex is linked to fructose). Leucrose is a disaccharide composed of glucose and fructose linked by an alpha-1,5 linkage. Wild type forms of glucosyltransferase enzymes generally contain (in the N-terminal to C-terminal direction) a signal peptide, a variable domain, a catalytic domain, and a glucan-binding domain. A gtf herein is classified under the glycoside hydrolase family 70 (GH70) according to the CAZy (Carbohydrate-Active EnZymes) database (Cantarel et al., Nucleic Acids Res. 37:D233-238, 2009).

The percentage of glycosidic linkages between the glucose monomer units of poly alpha-1,3-glucan used to prepare poly alpha-1,3-glucan ether compounds herein that are alpha-1,3 is at least about 50%, 60%, 70%, 80%, 90%, 95%, 96%, 97%, 98%, 99%, or 100% (or any integer value between 50% and 100%). In such embodiments, accordingly, poly alpha-1,3-glucan has less than about 50%, 40%, 30%, 20%, 10%, 5%, 4%, 3%, 2%, 1%, or 0% (or any integer value between 0% and 50%) of glycosidic linkages that are not alpha-1,3.

Poly alpha-1,3-glucan used to produce poly alpha-1,3-glucan ether compounds herein is preferably linear/unbranched. In certain embodiments, poly alpha-1,3-glucan has no branch points or less than about 10%, 9%, 8%, 7%, 6%, 5%, 4%, 3%, 2%, or 1% branch points as a percent of the glycosidic linkages in the polymer. Examples of branch points include alpha-1,6 branch points, such as those present in mutan polymer.

The terms "glycosidic linkage" and "glycosidic bond" are used interchangeably herein and refer to the type of covalent bond that joins a carbohydrate (sugar) molecule to another group such as another carbohydrate. The term "alpha-1,3-glycosidic linkage" as used herein refers to the type of covalent bond that joins alpha-D-glucose molecules to each other through carbons 1 and 3 on adjacent alpha-D-glucose rings. This linkage is illustrated in the poly alpha-1,3-glucan structure provided above. Herein, "alpha-D-glucose" will be referred to as "glucose".

The terms "poly alpha-1,3-glucan ether compound", "poly alpha-1,3-glucan ether", and "poly alpha-1,3-glucan ether derivative" are used interchangeably herein. A poly alpha-1,3-glucan ether compound herein can be represented by the structure:

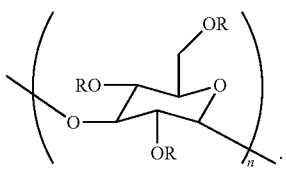

Regarding the formula of this structure, n can be at least 6, and each R can independently be a hydrogen atom (H) or a positively charged organic group. A poly alpha-1,3-glucan ether compound herein has a degree of substitution of about 0.05 to about 3.0. Given that poly alpha-1,3-glucan ether compounds herein have one or more types of positively charged organic groups, these compounds can be considered "cationic".

A poly alpha-1,3-glucan ether compound is termed an "ether" herein by virtue of comprising the substructure —$C_G$—O—C—, where "—$C_G$—" represents carbon 2, 4, or 6 of a glucose monomeric unit of a poly alpha-1,3-glucan ether compound, and where "—C—" is comprised in the positively charged organic group.

Poly alpha-1,3-glucan ether compounds disclosed herein are synthetic, man-made compounds.

A "positively charged organic group" group as used herein refers to a chain of one or more carbons ("carbon chain") that has one or more hydrogens substituted with another atom or functional group (i.e., a "substituted alkyl group"), where one or more of the substitutions is with a positively charged group. Where a positively charged organic group has a substitution in addition to a substitution with a positively charged group, such additional substitution may be with one or more hydroxyl groups, oxygen atoms (thereby forming an aldehyde or ketone group), alkyl groups, and/or additional positively charged groups. A positively charged organic group has a net positive charge since it comprises one or more positively charged groups.

The terms "positively charged group", "positively charged ionic group" and "cationic group" are used interchangeably herein. A positively charged group comprises a cation (a positively charged ion). Examples of positively charged groups include substituted ammonium groups, carbocation groups and acyl cation groups.

A composition that is "positively charged" herein typically has more protons than electrons and is repelled from other positively charged substances, but attracted to negatively charged substances.

The terms "substituted ammonium group", "substituted ammonium ion" and "substituted ammonium cation" are used interchangeably herein. A substituted ammonium group herein comprises structure I:

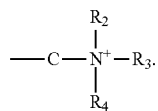

(I)

$R_2$, $R_3$ and $R_4$ in structure I each independently represent a hydrogen atom or an alkyl, aryl, cycloalkyl, aralkyl, or alkaryl group. The carbon atom (C) in structure I is part of the chain of one or more carbons ("carbon chain") of the positively charged organic group. The carbon atom is either directly ether-linked to a glucose monomer of poly alpha-1,3-glucan, or is part of a chain of two or more carbon atoms ether-linked to a glucose monomer of poly alpha-1,3-glucan. The carbon atom in structure I can be —$CH_2$—, —CH— (where a H is substituted with another group such as a hydroxy group), or —C— (where both H's are substituted).

A substituted ammonium group can be a "primary ammonium group", "secondary ammonium group", "tertiary ammonium group", or "quaternary ammonium" group, depending on the composition of $R_2$, $R_3$ and $R_4$ in structure I. A primary ammonium group herein refers to structure I in which each of $R_2$, $R_3$ and $R_4$ is a hydrogen atom (i.e., —C—$NH_3^+$). A secondary ammonium group herein refers to structure I in which each of $R_2$ and $R_3$ is a hydrogen atom and $R_4$ is an alkyl, aryl, or cycloalkyl group. A tertiary ammonium group herein refers to structure I in which $R_2$ is a hydrogen atom and each of $R_3$ and $R_4$ is an alkyl, aryl, or cycloalkyl group. A quaternary ammonium group herein refers to structure I in which each of $R_2$, $R_3$ and $R_4$ is an alkyl, aryl, or cycloalkyl group (i.e., none of $R_2$, $R_3$ and $R_4$ is a hydrogen atom).

A quaternary ammonium poly alpha-1,3-glucan ether herein can comprise a trialkyl ammonium group (where each of $R_2$, $R_3$ and $R_4$ is an alkyl group), for example. A trimethylammonium group is an example of a trialkyl ammonium group, where each of $R_2$, $R_3$ and $R_4$ is a methyl group. It would be understood that a fourth member (i.e., $R_1$) implied by "quaternary" in this nomenclature is the chain of one or more carbons of the positively charged organic group that is ether-linked to a glucose monomer of poly alpha-1,3-glucan.

An example of a quaternary ammonium poly alpha-1,3-glucan ether compound is trimethylammonium hydroxypropyl poly alpha-1,3-glucan. The positively charged organic group of this ether compound can be represented as structure II:

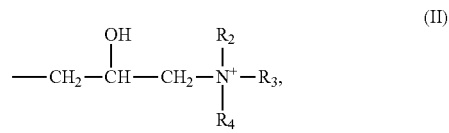

(II)

where each of $R_2$, $R_3$ and $R_4$ is a methyl group. Structure II is an example of a quaternary ammonium hydroxypropyl group.

A "hydroxy alkyl" group herein refers to a substituted alkyl group in which one or more hydrogen atoms of the alkyl group are substituted with a hydroxyl group. An example of a hydroxy alkyl group is a hydroxypropyl group; structure II comprises a hydroxypropyl group.

A "halide" herein refers to a compound comprising one or more halogen atoms (e.g., fluorine, chlorine, bromine, iodine). A halide herein can refer to a compound comprising one or more halide groups such as fluoride, chloride, bromide, or iodide. A halide group may serve as a reactive group of an etherification agent.

The terms "reaction", "reaction composition", and "etherification reaction" are used interchangeably herein and refer to a reaction comprising at least poly alpha-1,3-glucan and an etherification agent. These components are typically dissolved and/or mixed in an aqueous alkali hydroxide. A reaction is placed under suitable conditions (e.g., time, temperature) for the etherification agent to etherify one or more hydroxyl groups of the glucose units of poly alpha-1,3-glucan with a positively charged organic group, thereby yielding a poly alpha-1,3-glucan ether compound.

The term "alkaline conditions" herein refers to a solution or mixture pH of at least 11 or 12. Alkaline conditions can be prepared by any means known in the art, such as by dissolving an alkali hydroxide in a solution or mixture.

The terms "etherification agent" and "alkylation agent" are used interchangeably herein. An etherification agent herein refers to an agent that can be used to etherify one or more hydroxyl groups of one or more glucose units of poly alpha-1,3-glucan with a positively charged organic group. An etherification agent thus comprises a positively charged organic group.

The term "poly alpha-1,3-glucan slurry" herein refers to an aqueous mixture comprising the components of a glucosyltransferase enzymatic reaction such as poly alpha-1,3-glucan, sucrose, one or more glucosyltransferase enzymes, glucose and fructose. This composition is a slurry since the poly alpha-1,3-glucan is not dissolved therein.

The term "poly alpha-1,3-glucan wet cake" herein refers to poly alpha-1,3-glucan that has been separated from a slurry and washed with water or an aqueous solution. Poly alpha-1,3-glucan is not completely dried when preparing a wet cake.

The term "degree of substitution" (DoS) as used herein refers to the average number of hydroxyl groups substituted in each monomeric unit (glucose) of a poly alpha-1,3-glucan ether compound. Since there are three hydroxyl groups in each monomeric unit in poly alpha-1,3-glucan, the degree of substitution in a poly alpha-1,3-glucan ether compound herein can be no higher than 3.

The term "molar substitution" (M.S.) as used herein refers to the moles of a positively charged organic group per monomeric unit of a poly alpha-1,3-glucan ether compound. Alternatively, M.S. can refer to the average moles of etherification agent used to react with each monomeric unit in poly alpha-1,3-glucan (M.S. can thus describe the degree of derivatization of an etherification agent). It is noted that the M.S. value for poly alpha-1,3-glucan may have no upper limit. For example, when a positively charged organic group containing a hydroxyl group (e.g., hydroxyethyl or hydroxypropyl) has been etherified to poly alpha-1,3-glucan, the hydroxyl group of the organic group may undergo further reaction, thereby coupling more of the positively charged organic group to the poly alpha-1,3-glucan.

The term "crosslink" herein refers to a chemical bond, atom, or group of atoms that connects two adjacent atoms in one or more polymer molecules. It should be understood that, in a composition comprising crosslinked poly alpha-1,3-glucan ether, crosslinks can be between at least two poly alpha-1,3-glucan ether molecules (i.e., intermolecular crosslinks); there can also be intramolecular crosslinking. A "crosslinking agent" as used herein is an atom or compound that can create crosslinks.

An "aqueous composition" herein refers to a solution or mixture in which the solvent is at least about 20 wt % water, for example, and which comprises poly alpha-1,3-glucan and/or a poly alpha-1,3-glucan ether compound. Examples of aqueous compositions herein are aqueous solutions and hydrocolloids.

The terms "hydrocolloid" and "hydrogel" are used interchangeably herein. A hydrocolloid refers to a colloid system in which water is the dispersion medium. A "colloid" herein refers to a substance that is microscopically dispersed throughout another substance. Therefore, a hydrocolloid herein can also refer to a dispersion, emulsion, mixture, or solution of poly alpha-1,3-glucan and/or one or more poly alpha-1,3-glucan ether compounds in water or aqueous solution.

The term "aqueous solution" herein refers to a solution in which the solvent is water. Poly alpha-1,3-glucan and/or one or more poly alpha-1,3-glucan ether compounds herein can be dispersed, mixed, and/or dissolved in an aqueous solution. An aqueous solution can serve as the dispersion medium of a hydrocolloid herein.

The terms "dispersant" and "dispersion agent" are used interchangeably herein to refer to a material that promotes the formation and stabilization of a dispersion of one substance in another. A 'dispersion" herein refers to an aqueous composition comprising one or more particles (e.g., any ingredient of a personal care product, pharmaceutical product, food product, household product, or industrial product disclosed herein) that are scattered, or uniformly scattered, throughout the aqueous composition. It is believed that poly alpha-1,3-glucan and/or poly alpha-1,3-glucan ether compounds can act as dispersants in aqueous compositions disclosed herein.

The term "viscosity" as used herein refers to the measure of the extent to which a fluid or an aqueous composition such as a hydrocolloid resists a force tending to cause it to flow. Various units of viscosity that can be used herein include centipoise (cPs) and Pascal-second (Pa·s). A centipoise is one one-hundredth of a poise; one poise is equal to $0.100 \text{ kg} \cdot \text{m}^{-1} \cdot \text{s}^{-1}$. Thus, the terms "viscosity modifier" and "viscosity-modifying agent" as used herein refer to anything that can alter/modify the viscosity of a fluid or aqueous composition.

The term "shear thinning behavior" as used herein refers to a decrease in the viscosity of the hydrocolloid or aqueous solution as shear rate increases. The term "shear thickening behavior" as used herein refers to an increase in the viscosity of the hydrocolloid or aqueous solution as shear rate increases. "Shear rate" herein refers to the rate at which a progressive shearing deformation is applied to the hydrocolloid or aqueous solution. A shearing deformation can be applied rotationally.

The term "contacting" as used herein with respect to methods of increasing the viscosity of an aqueous composition refers to any action that results in bringing together an aqueous composition with poly alpha-1,3-glucan and/or a poly alpha-1,3-glucan ether compound. Contacting can be performed by any means known in the art, such as dissolving, mixing, shaking, or homogenization, for example.

The terms "fabric", "textile", and "cloth" are used interchangeably herein to refer to a woven material having a network of natural and/or artificial fibers. Such fibers can be thread or yarn, for example.

A "fabric care composition" herein is any composition suitable for treating fabric in some manner. Examples of such a composition include laundry detergents and fabric softeners.

The terms "heavy duty detergent" and "all-purpose detergent" are used interchangeably herein to refer to a detergent useful for regular washing of white and colored textiles at any temperature. The terms "low duty detergent" or "fine fabric detergent" are used interchangeably herein to refer to a detergent useful for the care of delicate fabrics such as viscose, wool, silk, microfiber or other fabric requiring special care. "Special care" can include conditions of using excess water, low agitation, and/or no bleach, for example.

An "oral care composition" herein is any composition suitable for treating an soft or hard surface in the oral cavity such as dental (teeth) and/or gum surfaces.

The term "adsorption" herein refers to the adhesion of a compound (e.g., poly alpha-1,3-glucan ether) to the surface of a material.

The "molecular weight" of poly alpha-1,3-glucan and poly alpha-1,3-glucan ether compounds herein can be represented as number-average molecular weight ($M_n$) or as weight-average molecular weight ($M_w$). Alternatively, molecular weight can be represented as Daltons, grams/mole, DPw (weight average degree of polymerization), or DPn (number average degree of polymerization). Various means are known in the art for calculating these molecular weight measurements, such as high-pressure liquid chromatography (HPLC), size exclusion chromatography (SEC), or gel permeation chromatography (GPC).

The terms "percent by volume", "volume percent", "vol %" and "v/v %" are used interchangeably herein. The percent by volume of a solute in a solution can be determined using the formula: [(volume of solute)/(volume of solution)]×100%.

The terms "percent by weight", "weight percentage (wt %)" and "weight-weight percentage (% w/w)" are used interchangeably herein. Percent by weight refers to the percentage of a material on a mass basis as it is comprised in a composition, mixture or solution.

The terms "increased", "enhanced" and "improved" are used interchangeably herein. These terms refer to a greater quantity or activity such as a quantity or activity slightly greater than the original quantity or activity, or a quantity or activity in large excess compared to the original quantity or activity, and including all quantities or activities in between. Alternatively, these terms may refer to, for example, a quantity or activity that is at least 1%, 2%, 3%, 4%, 5%, 6%, 7%, 8%, 9%, 10%, 20%, 30%, 40%, 50%, 60%, 70%, 80%, 90%, 100%, 125%, 150%, 175%, or 200% (or any integer between 1% and 200%) more than the quantity or activity for which the increased quantity or activity is being compared.

Development of new poly alpha-1,3-glucan ether derivatives and methods of preparing such derivatives is desirable given their potential utility in various applications. There is a keen interest in understanding the applicability of poly alpha-1,3-glucan ether derivatives as viscosity and rheology modifiers of hydrocolloid or aqueous compositions.

Embodiments of the disclosed invention concern a composition comprising a poly alpha-1,3-glucan ether compound represented by the structure:

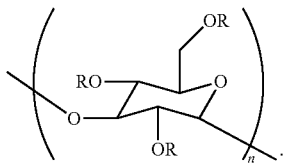

Regarding the formula of this structure, n can be at least 6, and each R can independently be an H or a positively charged organic group. Furthermore, the poly alpha-1,3-glucan ether compound has a degree of substitution of about 0.05 to about 3.0.

Significantly, a poly alpha-1,3-glucan ether compound of the invention can modify the viscosity of an aqueous solution to which it is added. This viscosity modification effect is often coupled with a rheology modification effect. Furthermore, when contacting a hydrocolloid or aqueous solution herein with a surface (e.g., fabric surface), one or more poly alpha-1,3-glucan ether compounds adsorb to the surface.

The degree of substitution (DoS) of a poly alpha-1,3-glucan ether compound disclosed herein can alternatively be about 0.2 to about 2.0. Alternatively still, the DoS can be at least about 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, or 3.0. It would be understood by those skilled in the art that since a poly alpha-1,3-glucan ether compound herein has a degree of substitution between about 0.05 to about 3.0, and by virtue of being an ether, the R groups of the compound cannot only be hydrogen.

The percentage of glycosidic linkages between the glucose monomer units of poly alpha-1,3-glucan ether compounds herein that are alpha-1,3 is at least about 50%, 60%, 70%, 80%, 90%, 95%, 96%, 97%, 98%, 99%, or 100% (or any integer between 50% and 100%). In such embodiments, accordingly, the compound has less than about 50%, 40%, 30%, 20%, 10%, 5%, 4%, 3%, 2%, 1%, or 0% (or any integer value between 0% and 50%) of glycosidic linkages that are not alpha-1,3.

The backbone of a poly alpha-1,3-glucan ether compound herein is preferably linear/unbranched. In certain embodiments, the compound has no branch points or less than about 10%, 9%, 8%, 7%, 6%, 5%, 4%, 3%, 2%, or 1% branch points as a percent of the glycosidic linkages in the polymer. Examples of branch points include alpha-1,6 branch points.

The formula of a poly alpha-1,3-glucan ether compound in certain embodiments can have an n value of at least 6. Alternatively, n can have a value of at least 25, 50, 75, 100, 150, 200, 250, 300, 350, 400, 450, 500, 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, or 4000 (or any integer between 25 and 4000), for example. The value of n in still other examples can be in a range of 25-250, 50-250, 75-250, 100-250, 150-250, 200-250, 25-200, 50-200, 75-200, 100-200, 150-200, 25-150, 50-150, 75-150, 100-150, 25-100, 50-100, 75-100, 25-75, 50-75, or 25-50.

The molecular weight of a poly alpha-1,3-glucan ether compound herein can be measured as number-average molecular weight ($M_n$) or as weight-average molecular weight ($M_w$). Alternatively, molecular weight can be measured in Daltons or grams/mole. It may also be useful to refer to the $DP_w$ (weight average degree of polymerization) or $DP_n$ (number average degree of polymerization) of the poly alpha-1,3-glucan polymer component of the compound.

The $M_n$ or $M_w$ of a poly alpha-1,3-glucan ether compound herein may be at least about 1000. Alternatively, the $M_n$ or $M_w$ can be at least about 1000 to about 600000. Alternatively still, the $M_n$ or $M_w$ can be at least about 2000, 3000, 4000, 5000, 6000, 7000, 8000, 9000, 10000, 15000, 20000, 25000, 30000, 35000, 40000, 45000, 50000, 75000, 100000, 150000, 200000, 250000, 300000, 350000, 400000, 450000, 500000, 550000, or 600000 (or any integer between 2000 and 600000), for example.

Each R group in the formula of a poly alpha-1,3-glucan ether compound herein can independently be an H or a positively charged organic group. As defined above, a positively charged organic group comprises a chain of one or more carbons having one or more hydrogens substituted with another atom or functional group, where one or more of the substitutions is with a positively charged group.

A positively charged group may be a substituted ammonium group, for example. Examples of substituted ammonium groups are primary, secondary, tertiary and quaternary ammonium groups. Structure I depicts a primary, secondary, tertiary or quaternary ammonium group, depending on the composition of $R_2$, $R_3$ and $R_4$ in structure I. Each of $R_2$, $R_3$ and $R_4$ in structure I independently represent a hydrogen atom or an alkyl, aryl, cycloalkyl, aralkyl, or alkaryl group. Alternatively, each of $R_2$, $R_3$ and $R_4$ in can independently represent a hydrogen atom or an alkyl group. An alkyl group herein can be a methyl, ethyl, propyl, butyl, pentyl, hexyl, heptyl, octyl, nonyl, or decyl group, for example. Where two or three of $R_2$, $R_3$ and $R_4$ are an alkyl group, they can be the same or different alkyl groups.

A "primary ammonium poly alpha-1,3-glucan ether compound" herein can comprise a positively charged organic group having an ammonium group. In this example, the positively charged organic group comprises structure I in which each of $R_2$, $R_3$ and $R_4$ is a hydrogen atom. A non-limiting example of such a positively charged organic group is represented by structure II when each of $R_2$, $R_3$ and $R_4$ is a hydrogen atom. An example of a primary ammonium poly alpha-1,3-glucan ether compound can be represented in shorthand as ammonium poly alpha-1,3-glucan ether. It would be understood that a first member (i.e., $R_1$) implied by "primary" in the above nomenclature is the chain of one or more carbons of the positively charged organic group that is ether-linked to a glucose monomer of poly alpha-1,3-glucan.

A "secondary ammonium poly alpha-1,3-glucan ether compound" herein can comprise a positively charged organic group having a monoalkylammonium group, for example. In this example, the positively charged organic group comprises structure I in which each of $R_2$ and $R_3$ is a hydrogen atom and $R_4$ is an alkyl group. A non-limiting example of such a positively charged organic group is represented by structure II when each of $R_2$ and $R_3$ is a hydrogen atom and $R_4$ is an alkyl group. An example of a secondary ammonium poly alpha-1,3-glucan ether compound can be represented in shorthand herein as monoalkylammonium poly alpha-1,3-glucan ether (e.g., monomethyl-, monoethyl-, monopropyl-, monobutyl-, monopentyl-, monohexyl-, monoheptyl-, monooctyl-, mononoyl- or monodecyl-ammonium poly alpha-1,3-glucan ether). It would be understood that a second member (i.e., $R_1$) implied by "secondary" in the above nomenclature is the chain of one or more carbons of the positively charged organic group that is ether-linked to a glucose monomer of poly alpha-1, 3-glucan.

A "tertiary ammonium poly alpha-1,3-glucan ether compound" herein can comprise a positively charged organic group having a dialkylammonium group, for example. In this example, the positively charged organic group comprises structure I in which $R_2$ is a hydrogen atom and each of $R_3$ and $R_4$ is an alkyl group. A non-limiting example of such a positively charged organic group is represented by structure II when $R_2$ is a hydrogen atom and each of $R_3$ and $R_4$ is an alkyl group. An example of a tertiary ammonium poly alpha-1,3-glucan ether compound can be represented in shorthand as dialkylammonium poly alpha-1,3-glucan ether (e.g., dimethyl-, diethyl-, dipropyl-, dibutyl-, dipentyl-, dihexyl-, diheptyl-, dioctyl-, dinonyl- or didecyl-ammonium poly alpha-1,3-glucan ether). It would be understood that a third member (i.e., $R_1$) implied by "tertiary" in the above nomenclature is the chain of one or more carbons of the positively charged organic group that is ether-linked to a glucose monomer of poly alpha-1,3-glucan.

A "quaternary ammonium poly alpha-1,3-glucan ether compound" herein can comprise a positively charged organic group having a trialkylammonium group, for example. In this example, the positively charged organic group comprises structure I in which each of $R_2$, $R_3$ and $R_4$ is an alkyl group. A non-limiting example of such a positively charged organic group is represented by structure II when each of $R_2$, $R_3$ and $R_4$ is an alkyl group. An example of a quaternary ammonium poly alpha-1,3-glucan ether compound can be represented in shorthand as trialkylammonium poly alpha-1,3-glucan ether (e.g., trimethyl-, triethyl-, tripropyl-, tributyl-, tripentyl-, trihexyl-, triheptyl-, trioctyl-, trinonyl- or tridecyl-ammonium poly alpha-1,3-glucan ether). It would be understood that a fourth member (i.e., $R_1$) implied by "quaternary" in the above nomenclature is the chain of one or more carbons of the positively charged organic group that is ether-linked to a glucose monomer of poly alpha-1,3-glucan.

Additional non-limiting examples of substituted ammonium groups that can serve as a positively charged group herein are represented in structure I when each of $R_2$, $R_3$ and $R_4$ independently represent a hydrogen atom; an alkyl group such as a methyl, ethyl, or propyl group; an aryl group such as a phenyl or naphthyl group; an aralkyl group such as a benzyl group; an alkaryl group; or a cycloalkyl group. Each of $R_2$, $R_3$ and $R_4$ may further comprise an amino group or a hydroxyl group, for example.

The nitrogen atom in a substituted ammonium group represented by structure I is bonded to a chain of one or more carbons as comprised in a positively charged organic group. This chain of one or more carbons ("carbon chain") is ether-linked to a glucose monomer of poly alpha-1,3-glucan, and may have one or more substitutions in addition to the substitution with the nitrogen atom of the substituted ammonium group. There can be 1, 2, 3, 4, 5, 6, 7, 8, 9 or 10 carbons, for example, in a carbon chain herein. To illustrate, the carbon chain of structure II is 3 carbon atoms in length.

Examples of a carbon chain of a positively charged organic group that do not have a substitution in addition to the substitution with a positively charged group include —$CH_2$—, —$CH_2CH_2$—, —$CH_2CH_2CH_2$—, —$CH_2CH_2CH_2CH_2$— and —$CH_2CH_2CH_2CH_2CH_2$—. In each of these examples, the first carbon atom of the chain is ether-linked to a glucose monomer of poly alpha-1,3-glucan, and the last carbon atom of the chain is linked to a positively charged group. Where the positively charged group is a substituted ammonium group, the last carbon atom of the chain in each of these examples is represented by the C in structure I.

Where a carbon chain of a positively charged organic group has a substitution in addition to a substitution with a positively charged group, such additional substitution may be with one or more hydroxyl groups, oxygen atoms (thereby forming an aldehyde or ketone group), alkyl groups (e.g., methyl, ethyl, propyl, butyl), and/or additional positively charged groups. A positively charged group is typically bonded to the terminal carbon atom of the carbon chain.

Examples of a carbon chain herein having one or more substitutions with a hydroxyl group include hydroxyalkyl (e.g., hydroxyethyl, hydroxypropyl, hydroxybutyl, hydroxypentyl) groups and dihydroxyalkyl (e.g., dihydroxyethyl, dihydroxypropyl, dihydroxybutyl, dihydroxypentyl) groups. Examples of hydroxyalkyl and dihydroxyalkyl (diol) carbon chains include —$CH(OH)$—, —$CH(OH)CH_2$—, —$C(OH)_2CH_2$—, —$CH_2CH(OH)CH_2$—, —$CH(OH)CH_2CH_2$—, —$CH(OH)CH(OH)CH_2$—, —$CH_2CH_2CH(OH)CH_2$—, —$CH_2CH(OH)CH_2CH_2$—, —$CH(OH)CH_2CH_2CH_2$—, —$CH_2CH(OH)CH(OH)CH_2$—, —$CH(OH)CH(OH)CH_2CH_2$— and —$CH(OH)CH_2CH(OH)CH_2$—. In each of these examples, the first carbon atom of the chain is ether-linked to a glucose monomer of poly alpha-1,3-glucan, and the last carbon atom of the chain is linked to a positively charged group. Where the positively charged group is a substituted ammonium group, the last carbon atom of the chain in each of these examples is represented by the C in structure I.

Examples of a carbon chain herein having one or more substitutions with an alkyl group include chains with one or more substituent methyl, ethyl and/or propyl groups.

Examples of methylalkyl groups include —CH(CH$_3$)CH$_2$CH$_2$— and —CH$_2$CH(CH$_3$)CH$_2$—, which are both propyl groups having a methyl substitution. In each of these examples, the first carbon atom of the chain is ether-linked to a glucose monomer of poly alpha-1,3-glucan, and the last carbon atom of the chain is linked to a positively charged group. Where the positively charged group is a substituted ammonium group, the last carbon atom of the chain in each of these examples is represented by the C in structure I.

Poly alpha-1,3-glucan ether compounds in certain embodiments disclosed herein may contain one type of positively charged organic group as an R group. For example, one or more positively charged organic groups ether-linked to the glucose monomer of poly alpha-1,3-glucan may be trimethylammonium hydroxypropyl groups (structure II); the R groups in this particular example would thus independently be hydrogen and trimethylammonium hydroxypropyl groups.

Alternatively, poly alpha-1,3-glucan ether compounds disclosed herein can contain two or more different types of positively charged organic groups as R groups.

Poly alpha-1,3-glucan ether compounds herein can comprise at least one nonionic organic group and at least one anionic group, for example. As another example, poly alpha-1,3-glucan ether compounds herein can comprise at least one nonionic organic group and at least one positively charged organic group.

The disclosed invention also concerns a hydrocolloid or aqueous solution comprising a poly alpha-1,3-glucan ether compound represented by the structure:

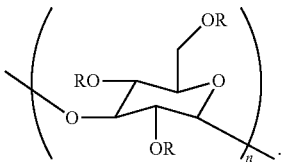

Regarding the formula of this structure, n can be at least 6, and each R can independently be an H or a positively charged organic group. Furthermore, the poly alpha-1,3-glucan ether compound has a degree of substitution of about 0.05 to about 3.0. The hydrocolloid or aqueous solution comprising the poly alpha-1,3-glucan ether compound has a viscosity of at least about 10 centipoise (cPs). The poly alpha-1,3-glucan ether compound in a hydrocolloid or aqueous solution can be any of the ether compounds disclosed herein.

Hydrocolloids or aqueous solutions comprising a poly alpha-1,3-glucan ether compound disclosed herein have a viscosity of at least about 10 cPs. Alternatively, a hydrocolloid or aqueous solution herein has a viscosity of at least about 100, 250, 500, 750, 1000, 1500, 2000, 2500, 3000, 3500, 4000, 4500, 5000, 5500, 6000, 6500, 7000, 7500, 8000, 8500, 9000, 9500, 10000, 10500, 11000, 12000, 13000, 14000, 15000, 20000, 30000, 40000, 50000, 60000, 70000, 80000, 90000, or 100000 cPs (or any integer between 100 and 100000 cPs), for example.

Viscosity can be measured with the hydrocolloid or aqueous solution at any temperature between about 3° C. to about 110° C. (or any integer between 3 and 110° C.), for example. Alternatively, viscosity can be measured at a temperature between about 4° C. to 30° C., or about 20° C. to 25° C. Viscosity can be measured at atmospheric pressure (about 760 torr) or any other higher or lower pressure.

The viscosity of a hydrocolloid or aqueous solution disclosed herein can be measured using a viscometer or rheometer, or using any other means known in the art. It would be understood by those skilled in the art that a rheometer can be used to measure the viscosity of those hydrocolloids and aqueous solutions of the invention that exhibit shear thinning behavior or shear thickening behavior (i.e., liquids with viscosities that vary with flow conditions). The viscosity of such embodiments can be measured at a rotational shear rate of about 10 to 1000 rpm (revolutions per minute) (or any integer between 10 and 1000 rpm), for example. Alternatively, viscosity can be measured at a rotational shear rate of about 10, 60, 150, 250, or 600 rpm.

The pH of a hydrocolloid or aqueous solution disclosed herein can be between about 2.0 to about 12.0. Alternatively, pH can be about 2.0, 3.0, 4.0, 5.0, 6.0, 7.0, 8.0, 9.0, 10.0, 11.0, 12.0; or between 5.0 to about 12.0; or between about 4.0 to about 8.0; or between about 3.0 and 11.0. In certain embodiments, the viscosity of the hydrocolloid or aqueous solution does not largely fluctuate at a pH between about 3.0 and 11.0.

An aqueous composition herein such as a hydrocolloid or aqueous solution can comprise a solvent having at least about 20 wt % water. In other embodiments, a solvent is at least about 30, 40, 50, 60, 70, 80, 90, or 100 wt % water (or any integer value between 20 and 100 wt %), for example.

A poly alpha-1,3-glucan ether compound disclosed herein can be present in a hydrocolloid or aqueous solution at a weight percentage (wt %) of at least about 0.01%, 0.05%, 0.1%, 0.2%, 0.3%, 0.4%, 0.5%, 0.6%, 0.7%, 0.8%, 0.9%, 1.0%, 1.2%, 1.4%, 1.6%, 1.8%, 2.0%, 2.5%, 3.0%, 3.5%, 4.0%, 4.5%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, or 30%, for example.

A hydrocolloid or aqueous solution herein can comprise other components in addition to one or more poly alpha-1,3-glucan ether compound. For example, the hydrocolloid or aqueous solution can comprise one or more salts such as a sodium salts (e.g., NaCl, Na$_2$SO$_4$). Other non-limiting examples of salts include those having (i) an aluminum, ammonium, barium, calcium, chromium (II or III), copper (I or II), iron (II or III), hydrogen, lead (II), lithium, magnesium, manganese (II or III), mercury (I or II), potassium, silver, sodium strontium, tin (II or IV), or zinc cation, and (ii) an acetate, borate, bromate, bromide, carbonate, chlorate, chloride, chlorite, chromate, cyanamide, cyanide, dichromate, dihydrogen phosphate, ferricyanide, ferrocyanide, fluoride, hydrogen carbonate, hydrogen phosphate, hydrogen sulfate, hydrogen sulfide, hydrogen sulfite, hydride, hydroxide, hypochlorite, iodate, iodide, nitrate, nitride, nitrite, oxalate, oxide, perchlorate, permanganate, peroxide, phosphate, phosphide, phosphite, silicate, stannate, stannite, sulfate, sulfide, sulfite, tartrate, or thiocyanate anion. Thus, any salt having a cation from (i) above and an anion from (ii) above can be in a hydrocolloid or aqueous solution, for example. A salt can be present in a hydrocolloid or aqueous solution at a wt % of about 0.01% to about 10.00% (or any hundredth increment between 0.01 and 10.00), for example.

A poly alpha-1,3-glucan ether compound herein is in a cationic form in the hydrocolloid or aqueous solution. The cationic groups of a poly alpha-1,3-glucan ether compound herein can interact with salt anions that may be present in a hydrocolloid or aqueous solution. Such salt anions can be any of those listed above in (ii) (e.g., chloride anion).

In alternative embodiments, a composition comprising poly alpha-1,3-glucan and/or a poly alpha-1,3-glucan ether compound herein can be non-aqueous (e.g., a dry composition). Examples of such embodiments include powders, granules, microcapsules, flakes, or any other form of particulate matter. Other example include larger compositions such as pellets, bars, kernels, beads, tablets, sticks, or other agglomerates. A non-aqueous or dry composition herein typically has less than 3, 2, 1, 0.5, or 0.1 wt % water comprised therein.

A poly alpha-1,3-glucan ether compound comprised in certain embodiments of the disclosed composition may be crosslinked using any means known in the art. Such crosslinks may be borate crosslinks, where the borate is from any boron-containing compound (e.g., boric acid, diborates, tetraborates, pentaborates, polymeric compounds such as Polybor®, polymeric compounds of boric acid, alkali borates), for example. Alternatively, crosslinks can be provided with polyvalent metals such as titanium or zirconium. Titanium crosslinks may be provided, for example, using titanium IV-containing compounds such as titanium ammonium lactate, titanium triethanolamine, titanium acetylacetonate, and polyhydroxy complexes of titanium. Zirconium crosslinks can be provided using zirconium IV-containing compounds such as zirconium lactate, zirconium carbonate, zirconium acetylacetonate, zirconium triethanolamine, zirconium diisopropylamine lactate and polyhydroxy complexes of zirconium, for example. Alternatively still, crosslinks can be provided with any crosslinking agent described in U.S. Pat. Nos. 4,462,917, 4,464,270, 4,477,360 and 4,799,550, which are all incorporated herein by reference. A crosslinking agent (e.g., borate) may be present in an aqueous composition herein at a concentration of about 0.2% to 20 wt %, or about 0.1, 0.2, 0.3, 0.4, 0.5, 1, 2, 3, 4, 5, 6, 7, 8, 9, 10, 15, or 20 wt %, for example.

A poly alpha-1,3-glucan ether compound disclosed herein that is crosslinked typically has a higher viscosity in an aqueous solution compared to its non-crosslinked counterpart. In addition, a crosslinked poly alpha-1,3-glucan ether compound can have increased shear thickening behavior compared to its non-crosslinked counterpart.

A composition herein may optionally contain one or more active enzymes. Non-limiting examples of suitable enzymes include proteases, cellulases, hemicellulases, peroxidases, lipolytic enzymes (e.g., metallolipolytic enzymes), xylanases, lipases, phospholipases, esterases (e.g., arylesterase, polyesterase), perhydrolases, cutinases, pectinases, pectate lyases, mannanases, keratinases, reductases, oxidases (e.g., choline oxidase), phenoloxidases, lipoxygenases, ligninases, pullulanases, tannases, pentosanases, malanases, beta-glucanases, arabinosidases, hyaluronidases, chondroitinases, laccases, metalloproteinases, amadoriases, glucoamylases, arabinofuranosidases, phytases, isomerases, transferases and amylases. If an enzyme(s) is included, it may be comprised in a composition herein at about 0.0001-0.1 wt % (e.g., 0.01-0.03 wt %) active enzyme (e.g., calculated as pure enzyme protein), for example.

One or more cellulase enzymes may optionally be comprised in a composition disclosed herein. A cellulase herein can have endocellulase activity (EC 3.2.1.4), exocellulase activity (EC 3.2.1.91), or cellobiase activity (EC 3.2.1.21). A cellulase herein is an "active cellulase" having activity under suitable conditions for maintaining cellulase activity; it is within the skill of the art to determine such suitable conditions. Besides being able to degrade cellulose, a cellulase in certain embodiments can also degrade cellulose ether derivatives such as carboxymethyl cellulose. Examples of cellulose ether derivatives which are expected to not be stable to cellulase are disclosed in U.S. Pat. Nos. 7,012,053, 7,056,880, 6,579,840, 7,534,759 and 7,576,048.

A cellulase herein may be derived from any microbial source, such as a bacteria or fungus. Chemically-modified cellulases or protein-engineered mutant cellulases are included. Suitable cellulases include, but are not limited to, cellulases from the genera Bacillus, Pseudomonas, Streptomyces, Trichoderma, Humicola, Fusarium, Thielavia and Acremonium. As other examples, a cellulase may be derived from Humicola insolens, Myceliophthora thermophila or Fusarium oxysporum; these and other cellulases are disclosed in U.S. Pat. Nos. 4,435,307, 5,648,263, 5,691,178, 5,776,757 and 7,604,974, which are all incorporated herein by reference. Exemplary Trichoderma reesei cellulases are disclosed in U.S. Pat. Nos. 4,689,297, 5,814,501, 5,324,649, and International Patent Appl. Publ. Nos. WO92/06221 and WO92/06165, all of which are incorporated herein by reference. Exemplary Bacillus cellulases are disclosed in U.S. Pat. No. 6,562,612, which is incorporated herein by reference. A cellulase, such as any of the foregoing, preferably is in a mature form lacking an N-terminal signal peptide. Commercially available cellulases useful herein include CELLUZYME® and CAREZYME® (Novozymes A/S); CLAZINASE® and PURADAX® HA (DuPont Industrial Biosciences), and KAC-500(B)® (Kao Corporation).

Alternatively, a cellulase herein may be produced by any means known in the art, such as described in U.S. Pat. Nos. 4,435,307, 5,776,757 and 7,604,974, which are incorporated herein by reference. For example, a cellulase may be produced recombinantly in a heterologous expression system, such as a microbial or fungal heterologous expression system. Examples of heterologous expression systems include bacterial (e.g., E. coli, Bacillus sp.) and eukaryotic systems. Eukaryotic systems can employ yeast (e.g., Pichia sp., Saccharomyces sp.) or fungal (e.g., Trichoderma sp. such as T. reesei, Aspergillus species such as A. niger) expression systems, for example.

One or more cellulases can be directly added as an ingredient when preparing the disclosed composition. Alternatively, one or more cellulases can be indirectly (inadvertently) provided in the disclosed composition. For example, cellulase can be provided in a composition herein by virtue of being present in a non-cellulase enzyme preparation used for preparing the composition. Cellulase in compositions in which cellulase is indirectly provided thereto can be present at about 0.1-10 ppb (e.g., less than 1 ppm), for example. A benefit of a composition herein, by virtue of employing a poly alpha-1,3-glucan ether compound instead of a cellulose ether compound, is that non-cellulase enzyme preparations that might have background cellulase activity can be used without concern that the desired effects of the glucan ether will be negated by the background cellulase activity.

A cellulase in certain embodiments can be thermostable. Cellulase thermostability refers to the ability of the enzyme to retain activity after exposure to an elevated temperature (e.g. about 60-70° C.) for a period of time (e.g., about 30-60 minutes). The thermostability of a cellulase can be measured by its half-life (t½) given in minutes, hours, or days, during which time period half the cellulase activity is lost under defined conditions.

A cellulase in certain embodiments can be stable to a wide range of pH values (e.g. neutral or alkaline pH such as pH of ~7.0 to ~11.0). Such enzymes can remain stable for a predetermined period of time (e.g., at least about 15 min., 30 min., or 1 hour) under such pH conditions.

At least one, two, or more cellulases may be included in the composition, for example. The total amount of cellulase in a composition herein typically is an amount that is suitable for the purpose of using cellulase in the composition (an "effective amount"). For example, an effective amount of cellulase in a composition intended for improving the feel and/or appearance of a cellulose-containing fabric is an amount that produces measurable improvements in the feel of the fabric (e.g., improving fabric smoothness and/or appearance, removing pills and fibrils which tend to reduce fabric appearance sharpness). As another example, an effective amount of cellulase in a fabric stonewashing composition herein is that amount which will provide the desired effect (e.g., to produce a worn and faded look in seams and on fabric panels). The amount of cellulase in a composition herein can also depend on the process parameters in which the composition is employed (e.g., equipment, temperature, time, and the like) and cellulase activity, for example. The effective concentration of cellulase in an aqueous composition in which a fabric is treated can be readily determined by a skilled artisan. In fabric care processes, cellulase can be present in an aqueous composition (e.g., wash liquor) in which a fabric is treated in a concentration that is minimally about 0.01-0.1 ppm total cellulase protein, or about 0.1-10 ppb total cellulase protein (e.g., less than 1 ppm), to maximally about 100, 200, 500, 1000, 2000, 3000, 4000, or 5000 ppm total cellulase protein, for example.

Poly alpha-1,3 glucan and/or poly alpha-1,3-glucan ethers herein are mostly or completely stable (resistant) to being degraded by cellulase. For example, the percent degradation of a poly alpha-1,3 glucan and/or poly alpha-1,3-glucan ether compound by one or more cellulases is less than 10%, 9%, 8%, 7%, 6%, 5%, 4%, 3%, 2%, or 1%, or is 0%. Such percent degradation can be determined, for example, by comparing the molecular weight of polymer before and after treatment with a cellulase for a period of time (e.g., ~24 hours).

Hydrocolloids and aqueous solutions of the invention can have shear thinning behavior or shear thickening behavior. Shear thinning behavior is observed as a decrease in viscosity of the hydrocolloid or aqueous solution as shear rate increases, whereas shear thickening behavior is observed as an increase in viscosity of the hydrocolloid or aqueous solution as shear rate increases. Modification of the shear thinning behavior or shear thickening behavior of an aqueous solution herein is due to the admixture of a poly alpha-1,3-glucan ether composition to the aqueous composition. Thus, one or more poly alpha-1,3-glucan ether compounds of the invention can be added to an aqueous liquid composition to modify its rheological profile (i.e., the flow properties of the aqueous liquid, solution, or mixture are modified). Also, one or more poly alpha-1,3-glucan ether compounds of the invention can be added to an aqueous composition to modify its viscosity.

The rheological properties of hydrocolloids and aqueous solutions of the invention can be observed by measuring viscosity over an increasing rotational shear rate (e.g., from about 10 rpm to about 250 rpm). For example, shear thinning behavior of a hydrocolloid or aqueous solution disclosed herein can be observed as a decrease in viscosity (cPs) by at least about 5%, 10%, 15%, 20%, 25%, 30%, 35%, 40%, 45%, 50%, 55%, 60%, 65%, 70%, 75%, 80%, 85%, 90%, or 95% (or any integer between 5% and 95%) as the rotational shear rate increases from about 10 rpm to 60 rpm, 10 rpm to 150 rpm, 10 rpm to 250 rpm, 60 rpm to 150 rpm, 60 rpm to 250 rpm, or 150 rpm to 250 rpm. As another example, shear thickening behavior of a hydrocolloid or aqueous solution disclosed herein can be observed as an increase in viscosity (cPs) by at least about 5%, 10%, 15%, 20%, 25%, 30%, 35%, 40%, 45%, 50%, 55%, 60%, 65%, 70%, 75%, 80%, 85%, 90%, 95%, 100%, 125%, 150%, 175%, or 200% (or any integer between 5% and 200%) as the rotational shear rate increases from about 10 rpm to 60 rpm, 10 rpm to 150 rpm, 10 rpm to 250 rpm, 60 rpm to 150 rpm, 60 rpm to 250 rpm, or 150 rpm to 250 rpm.

A hydrocolloid or aqueous solution disclosed herein can be in the form of, and/or comprised in, a personal care product, pharmaceutical product, food product, household product, or industrial product. Poly alpha-1,3-glucan and/or poly alpha-1,3-glucan ether compounds herein can be used as thickening agents and/or dispersion agents in each of these products. Such a thickening agent may be used in conjunction with one or more other types of thickening agents if desired, such as those disclosed in U.S. Pat. No. 8,541,041, the disclosure of which is incorporated herein by reference.

Personal care products herein are not particularly limited and include, for example, skin care compositions, cosmetic compositions, antifungal compositions, and antibacterial compositions. Personal care products herein may be in the form of, for example, lotions, creams, pastes, balms, ointments, pomades, gels, liquids, combinations of these and the like. The personal care products disclosed herein can include at least one active ingredient, if desired. An active ingredient is generally recognized as an ingredient that causes an intended pharmacological effect.

In certain embodiments, a skin care product can be applied to skin for addressing skin damage related to a lack of moisture. A skin care product may also be used to address the visual appearance of skin (e.g., reduce the appearance of flaky, cracked, and/or red skin) and/or the tactile feel of the skin (e.g., reduce roughness and/or dryness of the skin while improved the softness and subtleness of the skin). A skin care product typically may include at least one active ingredient for the treatment or prevention of skin ailments, providing a cosmetic effect, or for providing a moisturizing benefit to skin, such as zinc oxide, petrolatum, white petrolatum, mineral oil, cod liver oil, lanolin, dimethicone, hard fat, vitamin A, allantoin, calamine, kaolin, glycerin, or colloidal oatmeal, and combinations of these. A skin care product may include one or more natural moisturizing factors such as ceramides, hyaluronic acid, glycerin, squalane, amino acids, cholesterol, fatty acids, triglycerides, phospholipids, glycosphingolipids, urea, linoleic acid, glycosaminoglycans, mucopolysaccharide, sodium lactate, or sodium pyrrolidone carboxylate, for example. Other ingredients that may be included in a skin care product include, without limitation, glycerides, apricot kernel oil, canola oil, squalane, squalene, coconut oil, corn oil, jojoba oil, jojoba wax, lecithin, olive oil, safflower oil, sesame oil, shea butter, soybean oil, sweet almond oil, sunflower oil, tea tree oil, shea butter, palm oil, cholesterol, cholesterol esters, wax esters, fatty acids, and orange oil.

A personal care product herein can also be in the form of makeup, lipstick, mascara, rouge, foundation, blush, eyeliner, lip liner, lip gloss, other cosmetics, sunscreen, sun block, nail polish, mousse, hair spray, styling gel, nail conditioner, bath gel, shower gel, body wash, face wash, shampoo, hair conditioner (leave-in or rinse-out), cream rinse, hair dye, hair coloring product, hair shine product, hair serum, hair anti-frizz product, hair split-end repair product, lip balm, skin conditioner, cold cream, moisturizer, body spray, soap, body scrub, exfoliant, astringent, scruffing lotion, depilatory, permanent waving solution, antidandruff formulation, antiperspirant composition, deodorant, shaving product, pre-shaving product, after-shaving product, cleanser, skin gel, rinse, dentifrice composition, toothpaste, or mouthwash, for example.

A pharmaceutical product herein can be in the form of an emulsion, liquid, elixir, gel, suspension, solution, cream, or ointment, for example. Also, a pharmaceutical product herein can be in the form of any of the personal care products disclosed herein, such as an antibacterial or antifungal composition. A pharmaceutical product can further comprise one or more pharmaceutically acceptable carriers, diluents, and/or pharmaceutically acceptable salts. A poly alpha-1,3-glucan ether compound disclosed herein can also be used in capsules, encapsulants, tablet coatings, and as an excipients for medicaments and drugs.

Non-limiting examples of food products herein include vegetable, meat, and soy patties; reformed seafood; reformed cheese sticks; cream soups; gravies and sauces; salad dressing; mayonnaise; onion rings; jams, jellies, and syrups; pie filling; potato products such as French fries and extruded fries; batters for fried foods, pancakes/waffles and cakes; pet foods; beverages; frozen desserts; ice cream; cultured dairy products such as cottage cheese, yogurt, cheeses, and sour creams; cake icing and glazes; whipped topping; leavened and unleavened baked goods; and the like.

Poly alpha-1,3-glucan and/or poly alpha-1,3-glucan ether compounds, hydrocolloids and aqueous compositions disclosed herein can be used to provide one or more of the following physical properties to a food product (or any personal care product, pharmaceutical product, or industrial product): thickening, freeze/thaw stability, lubricity, moisture retention and release, texture, consistency, shape retention, emulsification, binding, suspension, dispersion, and gelation, for example. Poly alpha-1,3-glucan and/or poly alpha-1,3-glucan ether compounds disclosed herein can typically be used in a food product at a level of about 0.01 to about 5 wt %, for example.

A poly alpha-1,3-glucan and/or poly alpha-1,3-glucan ether compound disclosed herein can be comprised in a foodstuff or any other ingestible material (e.g., enteral pharmaceutical preparation) in an amount that provides the desired degree of thickening and/or dispersion. For example, the concentration or amount of a poly alpha-1,3-glucan and/or poly alpha-1,3-glucan ether compound in a product, on a weight basis, can be about 0.1-3 wt %, 0.1-4 wt %, 0.1-5 wt %, or 0.1-10 wt %.

A household and/or industrial product herein can be in the form of drywall tape-joint compounds; mortars; grouts; cement plasters; spray plasters; cement stucco; adhesives; pastes; wall/ceiling texturizers; binders and processing aids for tape casting, extrusion forming, injection molding and ceramics; spray adherents and suspending/dispersing aids for pesticides, herbicides, and fertilizers; fabric care products such as fabric softeners and laundry detergents; hard surface cleaners; air fresheners; polymer emulsions; gels such as water-based gels; surfactant solutions; paints such as water-based paints; protective coatings; adhesives; sealants and caulks; inks such as water-based ink; metal-working fluids; emulsion-based metal cleaning fluids used in electroplating, phosphatizing, galvanizing and/or general metal cleaning operations; hydraulic fluids (e.g., those used for fracking in downhole operations); and aqueous mineral slurries, for example.

Poly alpha-1,3-glucan and/or a poly alpha-1,3-glucan ether compound disclosed herein can be comprised in a personal care product, pharmaceutical product, household product, or industrial product in an amount that provides a desired degree of thickening or dispersion, for example. Examples of a concentration or amount of a poly alpha-1,3-glucan ether compound in a product, on a weight basis, can be about 0.1-3 wt %, 1-2 wt %, 1.5-2.5 wt %, 2.0 wt %, 0.1-4 wt %, 0.1-5 wt %, or 0.1-10 wt %.

Compositions disclosed herein can be in the form of a fabric care composition. A fabric care composition herein can be used for hand wash, machine wash and/or other purposes such as soaking and/or pretreatment of fabrics, for example. A fabric care composition may take the form of, for example, a laundry detergent; fabric conditioner; any wash-, rinse-, or dryer-added product; unit dose; or spray. Fabric care compositions in a liquid form may be in the form of an aqueous composition as disclosed herein. In other aspects, a fabric care composition can be in a dry form such as a granular detergent or dryer-added fabric softener sheet. Other non-limiting examples of fabric care compositions herein include: granular or powder-form all-purpose or heavy-duty washing agents; liquid, gel or paste-form all-purpose or heavy-duty washing agents; liquid or dry fine-fabric (e.g. delicates) detergents; cleaning auxiliaries such as bleach additives, "stain-stick", or pre-treatments; substrate-laden products such as dry and wetted wipes, pads, or sponges; sprays and mists.

A detergent composition herein may be in any useful form, e.g., as powders, granules, pastes, bars, unit dose, or liquid. A liquid detergent may be aqueous, typically containing up to about 70 wt % of water and 0 wt % to about 30 wt % of organic solvent. It may also be in the form of a compact gel type containing only about 30 wt % water.

A detergent composition herein typically comprises one or more surfactants, wherein the surfactant is selected from nonionic surfactants, anionic surfactants, cationic surfactants, ampholytic surfactants, zwitterionic surfactants, semipolar nonionic surfactants and mixtures thereof. In some embodiments, the surfactant is present at a level of from about 0.1% to about 60%, while in alternative embodiments the level is from about 1% to about 50%, while in still further embodiments the level is from about 5% to about 40%, by weight of the detergent composition. A detergent will usually contain 0 wt % to about 50 wt % of an anionic surfactant such as linear alkylbenzenesulfonate (LAS), alpha-olefinsulfonate (AOS), alkyl sulfate (fatty alcohol sulfate) (AS), alcohol ethoxysulfate (AEOS or AES), secondary alkanesulfonates (SAS), alpha-sulfo fatty acid methyl esters, alkyl- or alkenylsuccinic acid, or soap. In addition, a detergent composition may optionally contain 0 wt % to about 40 wt % of a nonionic surfactant such as alcohol ethoxylate (AEO or AE), carboxylated alcohol ethoxylates, nonylphenol ethoxylate, alkylpolyglycoside, alkyldimethylamineoxide, ethoxylated fatty acid monoethanolamide, fatty acid monoethanolamide, or polyhydroxy alkyl fatty acid amide (as described for example in WO92/06154, which is incorporated herein by reference).

A detergent composition herein typically comprises one or more detergent builders or builder systems. In some embodiments incorporating at least one builder, the cleaning compositions comprise at least about 1%, from about 3% to about 60%, or even from about 5% to about 40%, builder by weight of the composition. Builders include, but are not limited to, alkali metal, ammonium and alkanolammonium salts of polyphosphates, alkali metal silicates, alkaline earth and alkali metal carbonates, aluminosilicates, polycarboxylate compounds, ether hydroxypolycarboxylates, copolymers of maleic anhydride with ethylene or vinyl methyl ether, 1,3,5-trihydroxy benzene-2,4,6-trisulphonic acid, and carboxymethyloxysuccinic acid, various alkali metal, ammonium and substituted ammonium salts of polyacetic acids such as ethylenediamine tetraacetic acid and nitrilotriacetic acid, as well as polycarboxylates such as mellitic acid, succinic acid, citric acid, oxydisuccinic acid, polymaleic acid, benzene 1,3,5-tricarboxylic acid, carboxymethyloxysuccinic acid, and soluble salts thereof. Indeed, it is contemplated that any suitable builder will find use in various embodiments of the present invention. Examples of a detergent builder or complexing agent include zeolite, diphosphate, triphosphate, phosphonate, citrate, nitrilotriacetic acid (NTA), ethylenediaminetetraacetic acid (EDTA), diethylenetriaminepentaacetic acid (DTMPA), alkyl- or alkenylsuccinic acid, soluble silicates or layered silicates (e.g., SKS-6 from Hoechst). A detergent may also be unbuilt, i.e., essentially free of detergent builder.

In some embodiments, builders form water-soluble hardness ion complexes (e.g., sequestering builders), such as citrates and polyphosphates (e.g., sodium tripolyphosphate and sodium tripolyphospate hexahydrate, potassium tripolyphosphate, and mixed sodium and potassium tripolyphosphate, etc.). It is contemplated that any suitable builder will find use in the present invention, including those known in the art (See, e.g., EP2100949).

In some embodiments, builders for use herein include phosphate builders and non-phosphate builders. In some embodiments, the builder is a phosphate builder. In some embodiments, the builder is a non-phosphate builder. If present, builders are used in a level of from 0.1% to 80%, or from 5% to 60%, or from 10% to 50%, by weight of the composition. In some embodiments, the product comprises a mixture of phosphate and non-phosphate builders. Suitable phosphate builders include mono-phosphates, di-phosphates, tri-polyphosphates or oligomeric-polyphosphates, including the alkali metal salts of these compounds, including the sodium salts. In some embodiments, a builder can be sodium tripolyphosphate (STPP). Additionally, the composition can comprise carbonate and/or citrate, preferably citrate that helps to achieve a neutral pH composition. Other suitable non-phosphate builders include homopolymers and copolymers of polycarboxylic acids and their partially or completely neutralized salts, monomeric polycarboxylic acids and hydroxycarboxylic acids and their salts. In some embodiments, salts of the above mentioned compounds include ammonium and/or alkali metal salts, i.e., lithium, sodium, and potassium salts, including sodium salts. Suitable polycarboxylic acids include acyclic, alicyclic, heterocyclic and aromatic carboxylic acids, wherein in some embodiments, they can contain at least two carboxyl groups which are in each case separated from one another by, in some instances, no more than two carbon atoms.

A detergent composition herein can comprise at least one chelating agent. Suitable chelating agents include, but are not limited to copper, iron and/or manganese chelating agents and mixtures thereof. In embodiments in which at least one chelating agent is used, the composition comprises from about 0.1% to about 15%, or even from about 3.0% to about 10%, chelating agent by weight of the composition.

A detergent composition herein can comprise at least one deposition aid. Suitable deposition aids include, but are not limited to, polyethylene glycol, polypropylene glycol, polycarboxylate, soil release polymers such as polytelephthalic acid, clays such as kaolinite, montmorillonite, atapulgite, illite, bentonite, halloysite, and mixtures thereof.

A detergent composition herein can comprise one or more dye transfer inhibiting agents. Suitable polymeric dye transfer inhibiting agents include, but are not limited to, polyvinylpyrrolidone polymers, polyamine N-oxide polymers, copolymers of N-vinylpyrrolidone and N-vinylimidazole, polyvinyloxazolidones and polyvinylimidazoles or mixtures thereof. Additional dye transfer inhibiting agents include manganese phthalocyanine, peroxidases, polyvinylpyrrolidone polymers, polyamine N-oxide polymers, copolymers of N-vinylpyrrolidone and N-vinylimidazole, polyvinyloxazolidones and polyvinylimidazoles and/or mixtures thereof; chelating agents examples of which include ethylene-diamine-tetraacetic acid (EDTA); diethylene triamine penta methylene phosphonic acid (DTPMP); hydroxy-ethane diphosphonic acid (HEDP); ethylenediamine N,N'-disuccinic acid (EDDS); methyl glycine diacetic acid (MGDA); diethylene triamine penta acetic acid (DTPA); propylene diamine tetracetic acid (PDT A); 2-hydroxypyridine-N-oxide (HPNO); or methyl glycine diacetic acid (MGDA); glutamic acid N,N-diacetic acid (N,N-dicarboxymethyl glutamic acid tetrasodium salt (GLDA); nitrilotriacetic acid (NTA); 4,5-dihydroxy-m-benzenedisulfonic acid; citric acid and any salts thereof; N-hydroxyethylethylenediaminetriacetic acid (HEDTA), triethylenetetraaminehexaacetic acid (TTNA), N-hydroxyethyliminodiacetic acid (HEIDA), dihydroxyethylglycine (DHEG), ethylenediaminetetrapropionic acid (EDTP) and derivatives thereof, which can be used alone or in combination with any of the above. In embodiments in which at least one dye transfer inhibiting agent is used, a composition herein may comprise from about 0.0001% to about 10%, from about 0.01% to about 5%, or even from about 0.1% to about 3%, by weight of the composition.

A detergent composition herein can comprise silicates. In some of these embodiments, sodium silicates (e.g., sodium disilicate, sodium metasilicate, and/or crystalline phyllosilicates) find use. In some embodiments, silicates are present at a level of from about 1% to about 20% by weight of the composition. In some embodiments, silicates are present at a level of from about 5% to about 15% by weight of the composition.

A detergent composition herein can comprise dispersants. Suitable water-soluble organic materials include, but are not limited to the homo- or co-polymeric acids or their salts, in which the polycarboxylic acid comprises at least two carboxyl radicals separated from each other by not more than two carbon atoms.

A detergent composition herein may additionally comprise one or more enzymes. Examples of enzymes include proteases, cellulases, hemicellulases, peroxidases, lipolytic enzymes (e.g., metallolipolytic enzymes), xylanases, lipases, phospholipases, esterases (e.g., arylesterase, polyesterase), perhydrolases, cutinases, pectinases, pectate lyases, mannanases, keratinases, reductases, oxidases (e.g., choline oxidase, phenoloxidase), phenoloxidases, lipoxygenases, ligninases, pullulanases, tannases, pentosanases, malanases, beta-glucanases, arabinosidases, hyaluronidases, chondroitinases, laccases, metalloproteinases, amadoriases, glucoamylases, alpha-amylases, beta-amylases, galactosidases, galactanases, catalases, carageenases, hyaluronidases, keratinases, lactases, ligninases, peroxidases, phosphatases, polygalacturonases, pullulanases, rhamnogalactouronases, tannases, transglutaminases, xyloglucanases, xylosidases, metalloproteases, arabinofuranosidases, phytases, isomerases, transferases and/or amylases in any combination.

Any cellulase disclosed above is contemplated for use in the disclosed detergent compositions. Suitable cellulases include, but are not limited to *Humicola insolens* cellulases (See e.g., U.S. Pat. No. 4,435,307). Exemplary cellulases contemplated for use herein are those having color care benefit for a textile. Examples of cellulases that provide a color care benefit are disclosed in EP0495257, EP0531372, EP531315, WO96/11262, WO96/29397, WO94/07998; WO98/12307; WO95/24471, WO98/08940, and U.S. Pat. Nos. 5,457,046, 5,686,593 and 5,763,254, all of which are incorporated herein by reference. Examples of commercially available cellulases useful in a detergent include CELLUSOFT®, CELLUCLEAN®, CELLUZYME®, and CAREZYME® (Novo Nordisk A/S and Novozymes A/S); CLAZINASE®, PURADAX HA®, and REVITALENZ™ (DuPont Industrial Biosciences); BIOTOUCH® (AB Enzymes); and KAC-500(B)™ (Kao Corporation). Additional cellulases are disclosed in, e.g., U.S. Pat. Nos. 7,595, 182, 8,569,033, 7,138,263, 3,844,890, 4,435,307, 4,435, 307, and GB2095275.

In some embodiments of the present invention, the detergent compositions of the present invention can comprise one or more enzymes, each at a level from about 0.00001% to about 10% by weight of the composition and the balance of cleaning adjunct materials by weight of composition. In some other embodiments of the present invention, the detergent compositions also comprise each enzyme at a level of about 0.0001% to about 10%, about 0.001% to about 5%, about 0.001% to about 2%, about 0.005% to about 0.5%, enzyme by weight of the composition.

Suitable proteases include those of animal, vegetable or microbial origin. In some embodiments, microbial proteases are used. In some embodiments, chemically or genetically modified mutants are included. In some embodiments, the protease is a serine protease, preferably an alkaline microbial protease or a trypsin-like protease. Examples of alkaline proteases include subtilisins, especially those derived from *Bacillus* (e.g., subtilisin, *lentus, amyloliquefaciens*, subtilisin Carlsberg, subtilisin 309, subtilisin 147 and subtilisin 168). Additional examples include those mutant proteases described in U.S. Pat. Nos. RE34606, U.S Pat. Nos. 5,955, 340, 5,700,676, 6,312,936 and 6,482,628, all of which are incorporated herein by reference. Additional protease examples include, but are not limited to, trypsin (e.g., of porcine or bovine origin), and the *Fusarium* protease described in WO89/06270. In some embodiments, commercially available protease enzymes include, but are not limited to, MAXATASE®, MAXACAL™, MAXAPEM™, OPTICLEAN®, OPTIMASE®, PROPERASE®, PURAFECT®, PURAFECT® OXP, PURAMAX™, EXCELLASE™, PREFERENZ™ proteases (e.g. P100, P110, P280), EFFECTENZ™ proteases (e.g. P1000, P1050, P2000), EXCELLENZ™ proteases (e.g. P1000), ULTIMASE®, and PURAFAST™ (Genencor); ALCALASE®, SAVINASE®, PRIMASE®, DURAZYM™, POLARZYME®, OVOZYME®, KANNASE®, LIQUANASE®, NEUTRASE®, RELASE® and ESPERASE® (Novozymes); BLAP™ and BLAP™ variants (Henkel Kommanditgesellschaft auf Aktien, Duesseldorf, Germany), and KAP (B. alkalophilus subtilisin; Kao Corp., Tokyo, Japan). Various proteases are described in WO95/23221, WO92/21760, WO09/149200, WO09/149144, WO09/149145, WO11/072099, WO10/056640, WO10/056653, WO11/140364, WO12/151534, U.S. Pat. Publ. No. 2008/0090747, and U.S. Pat. Nos. 5,801,039, 5,340,735, 5,500, 364, 5,855,625, RE34606, 5955340, 5700676, 6312936 6482628, 8530219, and various other patents. In some further embodiments, neutral metalloproteases find use in the present invention, including but not limited to, the neutral metalloproteases described in WO1999014341, WO1999033960, WO1999014342, WO1999034003, WO2007044993, WO2009058303 and WO2009058661, all of which are incorporated herein by reference. Exemplary metalloproteases include nprE, the recombinant form of neutral metalloprotease expressed in *Bacillus subtilis* (See e.g., WO07/044993), and PMN, the purified neutral metalloprotease from *Bacillus amyloliquefaciens*.

Suitable mannanases include, but are not limited to, those of bacterial or fungal origin. Chemically or genetically modified mutants are included in some embodiments. Various mannanases are known which find use in the present invention (See, e.g., U.S. Pat. Nos. 6,566,114, 6,602,842, and 6,440,991, all of which are incorporated herein by reference). Commercially available mannanases that find use in the present invention include, but are not limited to MANNASTAR®, PURABRITE™, and MANNAWAY®.

Suitable lipases include those of bacterial or fungal origin. Chemically modified, proteolytically modified, or protein engineered mutants are included. Examples of useful lipases include those from the genera *Humicola* (e.g., *H. lanuginosa*, EP258068 and EP305216; *H. insolens*, WO96/13580), *Pseudomonas* (e.g., *P. alcaligenes* or *P. pseudoalcaligenes*, EP218272; *P. cepacia*, EP331376; *P. stutzeri*, GB1372034; *P. fluorescens* and *Pseudomonas* sp. strain SD 705, WO95/06720 and WO96/27002; *P. wisconsinensis*, WO96/12012); and *Bacillus* (e.g., *B. subtilis*, Dartois et al., Biochemica et Biophysica Acta 1131:253-360; *B. stearothermophilus*, JP64/744992; *B. pumilus*, WO91/16422). Furthermore, a number of cloned lipases find use in some embodiments of the present invention, including but not limited to, *Penicillium camembertii* lipase (See, Yamaguchi et al., Gene 103: 61-67 [1991]), Geotricum candidum lipase (See, Schimada et al., J. Biochem., 106:383-388 [1989]), and various *Rhizopus* lipases such as R. delemar lipase (See, Hass et al., Gene 109:117-113 [1991]), a R. niveus lipase (Kugimiya et al., Biosci. Biotech. Biochem. 56:716-719 [1992]) and *R. oryzae* lipase. Additional lipases useful herein include, for example, those disclosed in WO92/05249, WO94/01541, WO95/35381, WO96/00292, WO95/30744, WO94/25578, WO95/14783, WO95/22615, WO97/04079, WO97/07202, EP407225 and EP260105. Other types of lipase polypeptide enzymes such as cutinases also find use in some embodiments of the present invention, including but not limited to, cutinase derived from *Pseudomonas mendocina* (See, WO88/09367), and cutinase derived from *Fusarium solani pisi* (See, WO90/09446). Examples of certain commercially available lipase enzymes useful herein include M1 LIPASE™, LUMA FAST™, and LIPOMAX™ (Genencor); LIPEX®, LIPOLASE® and LIPOLASE® ULTRA (Novozymes); and LIPASE P™ "Amano" (Amano Pharmaceutical Co. Ltd., Japan).

Suitable polyesterases include, for example, those disclosed in WO01/34899, WO01/14629 and U.S. Pat. No. 6,933,140.

A detergent composition herein can also comprise 2,6-beta-D-fructan hydrolase, which is effective for removal/cleaning of certain biofilms present on household and/or industrial textiles/laundry.

Suitable amylases include, but are not limited to those of bacterial or fungal origin. Chemically or genetically modified mutants are included in some embodiments. Amylases that find use in the present invention, include, but are not limited to, alpha-amylases obtained from B. licheniformis (See e.g., GB1296839). Additional suitable amylases include those disclosed in WO9510603, WO9526397, WO9623874, WO9623873, WO9741213, WO9919467, WO0060060, WO0029560, WO9923211, WO9946399, WO0060058, WO0060059, WO9942567, WO0114532, WO02092797, WO0166712, WO0188107, WO0196537, WO0210355, WO9402597, WO0231124, WO9943793, WO9943794, WO2004113551, WO2005001064, WO2005003311, WO0164852, WO2006063594, WO2006066594, WO2006066596, WO2006012899, WO2008092919, WO2008000825, WO2005018336, WO2005066338, WO2009140504, WO2005019443, WO2010091221, WO2010088447, WO0134784, WO2006012902, WO2006031554, WO2006136161, WO2008101894, WO2010059413, WO2011098531, WO2011080352, WO2011080353, WO2011080354, WO2011082425, WO2011082429, WO2011076123, WO2011087836, WO2011076897, WO94183314, WO9535382, WO9909183, WO9826078, WO9902702, WO9743424, WO9929876, WO9100353, WO9605295, WO9630481, WO9710342, WO2008088493, WO2009149419, WO2009061381, WO2009100102, WO2010104675, WO2010117511, and WO2010115021, all of which are incorporated herein by reference.

Suitable amylases include, for example, commercially available amylases such as STAINZYME®, STAINZYME PLUS®, NATALASE®, DURAMYL®, TERMAMYL®, TERMAMYL ULTRA®, FUNGAMYL® and BAN™ (Novo Nordisk A/S and Novozymes A/S); RAPIDASE®, POWERASE®, PURASTAR® and PREFERENZ™ (DuPont Industrial Biosciences).

Suitable peroxidases/oxidases contemplated for use in the compositions include those of plant, bacterial or fungal origin. Chemically modified or protein engineered mutants are included. Examples of peroxidases useful herein include those from the genus *Coprinus* (e.g., *C. cinereus*, WO93/24618, WO95/10602, and WO98/15257), as well as those referenced in WO2005056782, WO2007106293, WO2008063400, WO2008106214, and WO2008106215. Commercially available peroxidases useful herein include, for example, GUARDZYME™ (Novo Nordisk A/S and Novozymes A/S).

In some embodiments, peroxidases are used in combination with hydrogen peroxide or a source thereof (e.g., a percarbonate, perborate or persulfate) in the compositions of the present invention. In some alternative embodiments, oxidases are used in combination with oxygen. Both types of enzymes are used for "solution bleaching" (i.e., to prevent transfer of a textile dye from a dyed fabric to another fabric when the fabrics are washed together in a wash liquor), preferably together with an enhancing agent (See e.g., WO94/12621 and WO95/01426). Suitable peroxidases/oxidases include, but are not limited to, those of plant, bacterial or fungal origin. Chemically or genetically modified mutants are included in some embodiments.

Enzymes that may be comprised in a detergent composition herein may be stabilized using conventional stabilizing agents, e.g., a polyol such as propylene glycol or glycerol; a sugar or sugar alcohol; lactic acid; boric acid or a boric acid derivative (e.g., an aromatic borate ester).

A detergent composition herein may contain about 1 wt % to about 65 wt % of a detergent builder or complexing agent such as zeolite, diphosphate, triphosphate, phosphonate, citrate, nitrilotriacetic acid (NTA), ethylenediaminetetraacetic acid (EDTA), diethylenetriaminepentaacetic acid (DTMPA), alkyl- or alkenylsuccinic acid, soluble silicates or layered silicates (e.g., SKS-6 from Hoechst). A detergent may also be unbuilt, i.e., essentially free of detergent builder.

A detergent composition in certain embodiments may comprise one or more other types of polymers in addition to a poly alpha-1,3-glucan and/or poly alpha-1,3-glucan ether compound. Examples of other types of polymers useful herein include carboxymethyl cellulose (CMC), poly(vinylpyrrolidone) (PVP), polyethylene glycol (PEG), poly (vinyl alcohol) (PVA), polycarboxylates such as polyacrylates, maleic/acrylic acid copolymers and lauryl methacrylate/acrylic acid copolymers.

A detergent composition herein may contain a bleaching system. For example, a bleaching system can comprise an $H_2O_2$ source such as perborate or percarbonate, which may be combined with a peracid-forming bleach activator such as tetraacetylethylenediamine (TAED) or nonanoyloxybenzenesulfonate (NOBS). Alternatively, a bleaching system may comprise peroxyacids (e.g., amide, imide, or sulfone type peroxyacids). Alternatively still, a bleaching system can be an enzymatic bleaching system comprising perhydrolase, for example, such as the system described in WO2005/056783.

A detergent composition herein may also contain conventional detergent ingredients such as fabric conditioners, clays, foam boosters, suds suppressors, anti-corrosion agents, soil-suspending agents, anti-soil redeposition agents, dyes, bactericides, tarnish inhibiters, optical brighteners, or perfumes. The pH of a detergent composition herein (measured in aqueous solution at use concentration) is usually neutral or alkaline (e.g., pH of about 7.0 to about 11.0).

Particular forms of detergent compositions that can be adapted for purposes disclosed herein are disclosed in, for example, US20090209445A1, US20100081598A1, U.S. Pat. No. 7,001,878B2, EP1504994B1, WO2001085888A2, WO2003089562A1, WO2009098659A1, WO2009098660A1, WO2009112992A1, WO2009124160A1, WO2009152031A1, WO2010059483A1, WO2010088112A1, WO2010090915A1, WO2010135238A1, WO2011094687A1, WO2011094690A1, WO2011127102A1, WO2011163428A1, WO2008000567A1, WO2006045391A1, WO2006007911A1, WO2012027404A1, E P174069061, WO2012059336A1, U.S. Pat. No. 6,730,646B1, WO2008087426A1, WO2010116139A1, and WO2012104613A1, all of which are incorporated herein by reference.

Laundry detergent compositions herein can optionally be heavy duty (all purpose) laundry detergent compositions. Exemplary heavy duty laundry detergent compositions comprise a detersive surfactant (10%-40% wt/wt), including an anionic detersive surfactant (selected from a group of linear or branched or random chain, substituted or unsubstituted alkyl sulphates, alkyl sulphonates, alkyl alkoxylated sulphate, alkyl phosphates, alkyl phosphonates, alkyl carboxylates, and/or mixtures thereof), and optionally non-ionic surfactant (selected from a group of linear or branched or random chain, substituted or unsubstituted alkyl alkoxylated alcohol, e.g., C8-C18 alkyl ethoxylated alcohols and/or C6-C12 alkyl phenol alkoxylates), where the weight ratio of anionic detersive surfactant (with a hydrophilic index (Hlc) of from 6.0 to 9) to non-ionic detersive surfactant is greater than 1:1. Suitable detersive surfactants also include cationic detersive surfactants (selected from a group of alkyl pyridinium compounds, alkyl quaternary ammonium compounds, alkyl quaternary phosphonium compounds, alkyl ternary sulphonium compounds, and/or mixtures thereof); zwitterionic and/or amphoteric detersive surfactants (selected from a group of alkanolamine sulpho-betaines); ampholytic surfactants; semi-polar non-ionic surfactants and mixtures thereof.

A detergent herein such as a heavy duty laundry detergent composition may optionally include, a surfactancy boosting polymer consisting of amphiphilic alkoxylated grease cleaning polymers (selected from a group of alkoxylated polymers having branched hydrophilic and hydrophobic properties, such as alkoxylated polyalkylenimines in the range of 0.05 wt %-10 wt %) and/or random graft polymers (typically comprising of hydrophilic backbone comprising monomers selected from the group consisting of: unsaturated C1-C6 carboxylic acids, ethers, alcohols, aldehydes, ketones, esters, sugar units, alkoxy units, maleic anhydride, saturated polyalcohols such as glycerol, and mixtures thereof; and hydrophobic side chain(s) selected from the group consisting of: C4-C25 alkyl group, polypropylene, polybutylene, vinyl ester of a saturated C1-C6 mono-carboxylic acid, C1-C6 alkyl ester of acrylic or methacrylic acid, and mixtures thereof.

A detergent herein such as a heavy duty laundry detergent composition may optionally include additional polymers such as soil release polymers (include anionically end-capped polyesters, for example SRP1, polymers comprising at least one monomer unit selected from saccharide, dicarboxylic acid, polyol and combinations thereof, in random or block configuration, ethylene terephthalate-based polymers and co-polymers thereof in random or block configuration, for example REPEL-O-TEX SF, SF-2 AND SRP6, TEXCARE SRA100, SRA300, SRN100, SRN170, SRN240, SRN300 AND SRN325, MARLOQUEST SL), anti-redeposition polymers (0.1 wt % to 10 wt %), include carboxylate polymers, such as polymers comprising at least one monomer selected from acrylic acid, maleic acid (or maleic anhydride), fumaric acid, itaconic acid, aconitic acid, mesaconic acid, citraconic acid, methylenemalonic acid, and any mixture thereof, vinylpyrrolidone homopolymer, and/or polyethylene glycol, molecular weight in the range of from 500 to 100,000 Da); and polymeric carboxylate (such as maleate/acrylate random copolymer or polyacrylate homopolymer).

A detergent herein such as a heavy duty laundry detergent composition may optionally further include saturated or unsaturated fatty acids, preferably saturated or unsaturated C12-C24 fatty acids (0 wt % to 10 wt %); deposition aids in addition to a poly alpha-1,3-glucan ether compound disclosed herein (examples for which include polysaccharides, cellulosic polymers, poly diallyl dimethyl ammonium halides (DADMAC), and co-polymers of DAD MAC with vinyl pyrrolidone, acrylamides, imidazoles, imidazolinium halides, and mixtures thereof, in random or block configuration, cationic guar gum, cationic starch, cationic polyacylamides, and mixtures thereof.

A detergent herein such as a heavy duty laundry detergent composition may optionally further include dye transfer inhibiting agents, examples of which include manganese phthalocyanine, peroxidases, polyvinylpyrrolidone polymers, polyamine N-oxide polymers, copolymers of N-vinylpyrrolidone and N-vinylimidazole, polyvinyloxazolidones and polyvinylimidazoles and/or mixtures thereof; chelating agents, examples of which include ethylene-diamine-tetraacetic acid (EDTA), diethylene triamine penta methylene phosphonic acid (DTPMP), hydroxy-ethane diphosphonic acid (HEDP), ethylenediamine N,N'-disuccinic acid (EDDS), methyl glycine diacetic acid (MGDA), diethylene triamine penta acetic acid (DTPA), propylene diamine tetracetic acid (PDTA), 2-hydroxypyridine-N-oxide (HPNO), or methyl glycine diacetic acid (MGDA), glutamic acid N,N-diacetic acid (N,N-dicarboxymethyl glutamic acid tetrasodium salt (GLDA), nitrilotriacetic acid (NTA), 4,5-dihydroxy-m-benzenedisulfonic acid, citric acid and any salts thereof, N-hydroxyethylethylenediaminetriacetic acid (HEDTA), triethylenetetraaminehexaacetic acid (TTNA), N-hydroxyethyliminodiacetic acid (HEIDA), dihydroxyethylglycine (DHEG), ethylenediaminetetrapropionic acid (EDTP), and derivatives thereof.

A detergent herein such as a heavy duty laundry detergent composition may optionally include silicone or fatty-acid based suds suppressors; hueing dyes, calcium and magnesium cations, visual signaling ingredients, anti-foam (0.001 wt % to about 4.0 wt %), and/or a structurant/thickener (0.01 wt % to 5 wt %) selected from the group consisting of diglycerides and triglycerides, ethylene glycol distearate, microcrystalline cellulose, microfiber cellulose, biopolymers, xanthan gum, gellan gum, and mixtures thereof). Such structurant/thickener would be in addition to the one or more poly alpha-1,3-glucan compounds comprised in the detergent.

A detergent herein can be in the form of a heavy duty dry/solid laundry detergent composition, for example. Such a detergent may include: (i) a detersive surfactant, such as any anionic detersive surfactant disclosed herein, any nonionic detersive surfactant disclosed herein, any cationic detersive surfactant disclosed herein, any zwitterionic and/or amphoteric detersive surfactant disclosed herein, any ampholytic surfactant, any semi-polar non-ionic surfactant, and mixtures thereof; (ii) a builder, such as any phosphate-free builder (e.g., zeolite builders in the range of 0 wt % to less than 10 wt %), any phosphate builder (e.g., sodium tri-polyphosphate in the range of 0 wt % to less than 10 wt %), citric acid, citrate salts and nitrilotriacetic acid, any silicate salt (e.g., sodium or potassium silicate or sodium meta-silicate in the range of 0 wt % to less than 10 wt %); any carbonate salt (e.g., sodium carbonate and/or sodium bicarbonate in the range of 0 wt % to less than 80 wt %), and mixtures thereof; (iii) a bleaching agent, such as any photobleach (e.g., sulfonated zinc phthalocyanines, sulfonated aluminum phthalocyanines, xanthenes dyes, and mixtures thereof), any hydrophobic or hydrophilic bleach activator (e.g., dodecanoyl oxybenzene sulfonate, decanoyl oxybenzene sulfonate, decanoyl oxybenzoic acid or salts thereof, 3,5,5-trimethy hexanoyl oxybenzene sulfonate, tetraacetyl ethylene diamine-TAED, nonanoyloxybenzene sulfonate-NOBS, nitrile quats, and mixtures thereof), any source of hydrogen peroxide (e.g., inorganic perhydrate salts, examples of which include mono or tetra hydrate sodium salt of perborate, percarbonate, persulfate, perphosphate, or persilicate), any preformed hydrophilic and/or hydrophobic peracids (e.g., percarboxylic acids and salts, percarbonic acids and salts, perimidic acids and salts, peroxymonosulfuric acids and salts, and mixtures thereof); and/or (iv) any other components such as a bleach catalyst (e.g., imine bleach boosters examples of which include iminium cations and polyions, iminium zwitterions, modified amines, modified amine oxides, N-sulphonyl imines, N-phosphonyl imines, N-acyl imines, thiadiazole dioxides, perfluoroimines, cyclic sugar ketones, and mixtures thereof), and a metal-containing bleach catalyst (e.g., copper, iron, titanium, ruthenium, tungsten, molybdenum, or manganese cations along with an auxiliary metal cations such as zinc or aluminum and a sequestrate such as EDTA, ethylenediaminetetra(methylenephosphonic acid).

Compositions disclosed herein can be in the form of a dishwashing detergent composition. Examples of dishwashing detergents include automatic dishwashing detergents (typically used in dishwasher machines) and hand-washing dish detergents. A dishwashing detergent composition can be in any dry or liquid/aqueous form as disclosed herein, for example. Components that may be included in certain embodiments of a dishwashing detergent composition include, for example, one or more of a phosphate; oxygenor chlorine-based bleaching agent; non-ionic surfactant; alkaline salt (e.g., metasilicates, alkali metal hydroxides, sodium carbonate); any active enzyme disclosed herein; anti-corrosion agent (e.g., sodium silicate); anti-foaming agent; additives to slow down the removal of glaze and patterns from ceramics; perfume; anti-caking agent (in granular detergent); starch (in tablet-based detergents); gelling agent (in liquid/gel based detergents); and/or sand (powdered detergents).

Dishwashing detergents such as an automatic dishwasher detergent or liquid dishwashing detergent can comprise (i) a non-ionic surfactant, including any ethoxylated non-ionic surfactant, alcohol alkoxylated surfactant, epoxy-capped poly(oxyalkylated) alcohol, or amine oxide surfactant present in an amount from 0 to 10 wt %; (ii) a builder, in the range of about 5-60 wt %, including any phosphate builder (e.g., mono-phosphates, di-phosphates, tri-polyphosphates, other oligomeric-polyphosphates, sodium tripolyphosphate-STPP), any phosphate-free builder (e.g., amino acid-based compounds including methyl-glycine-diacetic acid [MGDA] and salts or derivatives thereof, glutamic-N,N-diacetic acid [GLDA] and salts or derivatives thereof, iminodisuccinic acid (IDS) and salts or derivatives thereof, carboxy methyl inulin and salts or derivatives thereof, nitrilotriacetic acid [NTA], diethylene triamine penta acetic acid [DTPA], B-alaninediacetic acid [B-ADA] and salts thereof), homopolymers and copolymers of poly-carboxylic acids and partially or completely neutralized salts thereof, monomeric polycarboxylic acids and hydroxycarboxylic acids and salts thereof in the range of 0.5 wt % to 50 wt %, or sulfonated/carboxylated polymers in the range of about 0.1 wt % to about 50 wt %; (iii) a drying aid in the range of about 0.1 wt % to about 10 wt % (e.g., polyesters, especially anionic polyesters, optionally together with further monomers with 3 to 6 functionalities—typically acid, alcohol or ester functionalities which are conducive to polycondensation, polycarbonate-, polyurethane- and/or polyurea-polyorganosiloxane compounds or precursor compounds thereof, particularly of the reactive cyclic carbonate and urea type); (iv) a silicate in the range from about 1 wt % to about 20 wt % (e.g., sodium or potassium silicates such as sodium disilicate, sodium meta-silicate and crystalline phyllosilicates); (v) an inorganic bleach (e.g., perhydrate salts such as perborate, percarbonate, perphosphate, persulfate and persilicate salts) and/or an organic bleach (e.g., organic peroxyacids such as diacyl- and tetraacylperoxides, especially diperoxydodecanedioic acid, diperoxytetradecanedioic acid, and diperoxyhexadecanedioic acid); (vi) a bleach activator (e.g., organic peracid precursors in the range from about 0.1 wt % to about 10 wt %) and/or bleach catalyst (e.g., manganese triazacyclononane and related complexes; Co, Cu, Mn, and Fe bispyridylamine and related complexes; and pentamine acetate cobalt(III) and related complexes); (vii) a metal care agent in the range from about 0.1 wt % to 5 wt % (e.g., benzatriazoles, metal salts and complexes, and/or silicates); and/or (viii) any active enzyme disclosed herein in the range from about 0.01 to 5.0 mg of active enzyme per gram of automatic dishwasher detergent composition, and an enzyme stabilizer component (e.g., oligosaccharides, polysaccharides, and inorganic divalent metal salts).

Various examples of detergent formulations comprising at least one poly alpha-1,3-glucan ether compound (e.g., a quaternary ammonium poly alpha-1,3-glucan such as trimethylammonium hydroxypropyl poly alpha-1,3-glucan) are disclosed below (1-19):

1) A detergent composition formulated as a granulate having a bulk density of at least 600 g/L comprising: linear alkylbenzenesulfonate (calculated as acid) at about 7-12 wt %; alcohol ethoxysulfate (e.g., C12-18 alcohol, 1-2 ethylene oxide [EO]) or alkyl sulfate (e.g., C16-18) at about 1-4 wt %; alcohol ethoxylate (e.g., C14-15 alcohol) at about 5-9 wt %; sodium carbonate at about 14-20 wt %; soluble silicate (e.g., $Na_2O$ $2SiO_2$) at about 2-6 wt %; zeolite (e.g., $NaAlSiO_4$) at about 15-22 wt %; sodium sulfate at about 0-6 wt %; sodium citrate/citric acid at about 0-15 wt %; sodium perborate at about 11-18 wt %; TAED at about 2-6 wt %; poly alpha-1,3-glucan ether up to about 2 wt %; other polymers (e.g., maleic/acrylic acid copolymer, PVP, PEG) at about 0-3 wt %; optionally an enzyme(s) (calculated as pure enzyme protein) at about 0.0001-0.1 wt %; and minor ingredients (e.g., suds suppressors, perfumes, optical brightener, photobleach) at about 0-5 wt %.

2) A detergent composition formulated as a granulate having a bulk density of at least 600 g/L comprising: linear alkylbenzenesulfonate (calculated as acid) at about 6-11 wt %; alcohol ethoxysulfate (e.g., C12-18 alcohol, 1-2 EO) or alkyl sulfate (e.g., C16-18) at about 1-3 wt %; alcohol ethoxylate (e.g., C14-15 alcohol) at about 5-9 wt %; sodium carbonate at about 15-21 wt %; soluble silicate (e.g., $Na_2O$ $2SiO_2$) at about 1-4 wt %; zeolite (e.g., $NaAlSiO_4$) at about 24-34 wt %; sodium sulfate at about 4-10 wt %; sodium citrate/citric acid at about 0-15 wt %; sodium perborate at about 11-18 wt %; TAED at about 2-6 wt %; poly alpha-1,3-glucan ether up to about 2 wt %; other polymers (e.g., maleic/acrylic acid copolymer, PVP, PEG) at about 1-6 wt %; optionally an enzyme(s) (calculated as pure enzyme protein) at about 0.0001-0.1 wt %; and minor ingredients (e.g., suds suppressors, perfumes, optical brightener, photobleach) at about 0-5 wt %.

3) A detergent composition formulated as a granulate having a bulk density of at least 600 g/L comprising: linear alkylbenzenesulfonate (calculated as acid) at about 5-9 wt %; alcohol ethoxysulfate (e.g., C12-18 alcohol, 7 EO) at about 7-14 wt %; soap as fatty acid (e.g., C16-22 fatty acid) at about 1-3 wt %; sodium carbonate at about 10-17 wt %; soluble silicate (e.g., $Na_2O$ $2SiO_2$) at about 3-9 wt %; zeolite (e.g., $NaAlSiO_4$) at about 23-33 wt %; sodium sulfate at about 0-4 wt %; sodium perborate at about 8-16 wt %; TAED at about 2-8 wt %; phosphonate (e.g., EDTMPA) at about 0-1 wt %; poly alpha-1,3-glucan ether up to about 2 wt %; other polymers (e.g., maleic/acrylic acid copolymer, PVP, PEG) at about 0-3 wt %; optionally an enzyme(s) (calculated as pure enzyme protein) at about 0.0001-0.1 wt %; and minor ingredients (e.g., suds suppressors, perfumes, optical brightener) at about 0-5 wt %.

4) A detergent composition formulated as a granulate having a bulk density of at least 600 g/L comprising: linear alkylbenzenesulfonate (calculated as acid) at about 8-12 wt %; alcohol ethoxylate (e.g., C12-18 alcohol, 7 EO) at about 10-25 wt %; sodium carbonate at about 14-22 wt %; soluble silicate (e.g., $Na_2O$ $2SiO_2$) at about 1-5 wt %; zeolite (e.g., $NaAlSiO_4$) at about 25-35 wt %; sodium sulfate at about 0-10 wt %; sodium perborate at about 8-16 wt %; TAED at about 2-8 wt %; phosphonate (e.g., EDTMPA) at about 0-1 wt %; poly alpha-1,3-glucan ether up to about 2 wt %; other polymers (e.g., maleic/acrylic acid copolymer, PVP, PEG) at about 1-3 wt %; optionally an enzyme(s) (calculated as pure enzyme protein) at about 0.0001-0.1 wt %; and minor ingredients (e.g., suds suppressors, perfumes) at about 0-5 wt %.

5) An aqueous liquid detergent composition comprising: linear alkylbenzenesulfonate (calculated as acid) at about 15-21 wt %; alcohol ethoxylate (e.g., C12-18 alcohol, 7 EO; or C12-15 alcohol, 5 EO) at about 12-18 wt %; soap as fatty acid (e.g., oleic acid) at about 3-13 wt %; alkenylsuccinic acid (C12-14) at about 0-13 wt %; aminoethanol at about 8-18 wt %; citric acid at about 2-8 wt %; phosphonate at about 0-3 wt %; poly alpha-1,3-glucan ether up to about 2 wt %; other polymers (e.g., PVP, PEG) at about 0-3 wt %; borate at about 0-2 wt %; ethanol at about 0-3 wt %; propylene glycol at about 8-14 wt %; optionally an enzyme(s) (calculated as pure enzyme protein) at about 0.0001-0.1 wt %; and minor ingredients (e.g., dispersants, suds suppressors, perfume, optical brightener) at about 0-5 wt %.

6) An aqueous structured liquid detergent composition comprising: linear alkylbenzenesulfonate (calculated as acid) at about 15-21 wt %; alcohol ethoxylate (e.g., C12-18 alcohol, 7 EO; or C12-15 alcohol, 5 EO) at about 3-9 wt %; soap as fatty acid (e.g., oleic acid) at about 3-10 wt %; zeolite (e.g., $NaAlSiO_4$) at about 14-22 wt %; potassium citrate about 9-18 wt %; borate at about 0-2 wt %; poly alpha-1,3-glucan ether up to about 2 wt %; other polymers (e.g., PVP, PEG) at about 0-3 wt %; ethanol at about 0-3 wt %; anchoring polymers (e.g., lauryl methacrylate/acrylic acid copolymer, molar ratio 25:1, MW 3800) at about 0-3 wt %; glycerol at about 0-5 wt %; optionally an enzyme(s) (calculated as pure enzyme protein) at about 0.0001-0.1 wt %; and minor ingredients (e.g., dispersants, suds suppressors, perfume, optical brightener) at about 0-5 wt %.

7) A detergent composition formulated as a granulate having a bulk density of at least 600 g/L comprising: fatty alcohol sulfate at about 5-10 wt %, ethoxylated fatty acid monoethanolamide at about 3-9 wt %; soap as fatty acid at about 0-3 wt %; sodium carbonate at about 5-10 wt %; soluble silicate (e.g., $Na_2O\ 2SiO_2$) at about 1-4 wt %; zeolite (e.g., $NaAlSiO_4$) at about 20-40 wt %; sodium sulfate at about 2-8 wt %; sodium perborate at about 12-18 wt %; TAED at about 2-7 wt %; poly alpha-1,3-glucan ether up to about 2 wt %; other polymers (e.g., maleic/acrylic acid copolymer, PEG) at about 1-5 wt %; optionally an enzyme(s) (calculated as pure enzyme protein) at about 0.0001-0.1 wt %; and minor ingredients (e.g., optical brightener, suds suppressors, perfumes) at about 0-5 wt %.

8) A detergent composition formulated as a granulate comprising: linear alkylbenzenesulfonate (calculated as acid) at about 8-14 wt %; ethoxylated fatty acid monoethanolamide at about 5-11 wt %; soap as fatty acid at about 0-3 wt %; sodium carbonate at about 4-10 wt %; soluble silicate (e.g., $Na_2O\ 2SiO_2$) at about 1-4 wt %; zeolite (e.g., $NaAlSiO_4$) at about 30-50 wt %; sodium sulfate at about 3-11 wt %; sodium citrate at about 5-12 wt %; poly alpha-1,3-glucan ether up to about 2 wt %; other polymers (e.g., PVP, maleic/acrylic acid copolymer, PEG) at about 1-5 wt %; optionally an enzyme(s) (calculated as pure enzyme protein) at about 0.0001-0.1 wt %; and minor ingredients (e.g., suds suppressors, perfumes) at about 0-5 wt %.

9) A detergent composition formulated as a granulate comprising: linear alkylbenzenesulfonate (calculated as acid) at about 6-12 wt %; nonionic surfactant at about 1-4 wt %; soap as fatty acid at about 2-6 wt %; sodium carbonate at about 14-22 wt %; zeolite (e.g., $NaAlSiO_4$) at about 18-32 wt %; sodium sulfate at about 5-20 wt %; sodium citrate at about 3-8 wt %; sodium perborate at about 4-9 wt %; bleach activator (e.g., NOBS or TAED) at about 1-5 wt %; poly alpha-1,3-glucan ether up to about 2 wt %; other polymers (e.g., polycarboxylate or PEG) at about 1-5 wt %; optionally an enzyme(s) (calculated as pure enzyme protein) at about 0.0001-0.1 wt %; and minor ingredients (e.g., optical brightener, perfume) at about 0-5 wt %.

10) An aqueous liquid detergent composition comprising: linear alkylbenzenesulfonate (calculated as acid) at about 15-23 wt %; alcohol ethoxysulfate (e.g., C12-15 alcohol, 2-3 EO) at about 8-15 wt %; alcohol ethoxylate (e.g., C12-15 alcohol, 7 EO; or C12-15 alcohol, 5 EO) at about 3-9 wt %; soap as fatty acid (e.g., lauric acid) at about 0-3 wt %; aminoethanol at about 1-5 wt %; sodium citrate at about 5-10 wt %; hydrotrope (e.g., sodium toluenesulfonate) at about 2-6 wt %; borate at about 0-2 wt %; poly alpha-1,3-glucan ether up to about 1 wt %; ethanol at about 1-3 wt %; propylene glycol at about 2-5 wt %; optionally an enzyme(s) (calculated as pure enzyme protein) at about 0.0001-0.1 wt %; and minor ingredients (e.g., dispersants, perfume, optical brighteners) at about 0-5 wt %.

11) An aqueous liquid detergent composition comprising: linear alkylbenzenesulfonate (calculated as acid) at about 20-32 wt %; alcohol ethoxylate (e.g., C12-15 alcohol, 7 EO; or C12-15 alcohol, 5 EO) at about 6-12 wt %; aminoethanol at about 2-6 wt %; citric acid at about 8-14 wt %; borate at about 1-3 wt %; poly alpha-1,3-glucan ether up to about 2 wt %; ethanol at about 1-3 wt %; propylene glycol at about 2-5 wt %; other polymers (e.g., maleic/acrylic acid copolymer, anchoring polymer such as lauryl methacrylate/acrylic acid copolymer) at about 0-3 wt %; glycerol at about 3-8 wt %; optionally an enzyme(s) (calculated as pure enzyme protein) at about 0.0001-0.1 wt %; and minor ingredients (e.g., hydrotropes, dispersants, perfume, optical brighteners) at about 0-5 wt %.

12) A detergent composition formulated as a granulate having a bulk density of at least 600 g/L comprising: anionic surfactant (e.g., linear alkylbenzenesulfonate, alkyl sulfate, alpha-olefinsulfonate, alpha-sulfo fatty acid methyl esters, alkanesulfonates, soap) at about 25-40 wt %; nonionic surfactant (e.g., alcohol ethoxylate) at about 1-10 wt %; sodium carbonate at about 8-25 wt %; soluble silicate (e.g., $Na_2O\ 2SiO_2$) at about 5-15 wt %; sodium sulfate at about 0-5 wt %; zeolite ($NaAlSiO_4$) at about 15-28 wt %; sodium perborate at about 0-20 wt %; bleach activator (e.g., TAED or NOBS) at about 0-5 wt %; poly alpha-1,3-glucan ether up to about 2 wt %; optionally an enzyme(s) (calculated as pure enzyme protein) at about 0.0001-0.1 wt %; and minor ingredients (e.g., perfume, optical brighteners) at about 0-3 wt %.

13) Detergent compositions as described in (1)-(12) above, but in which all or part of the linear alkylbenzenesulfonate is replaced by C12-C18 alkyl sulfate.

14) A detergent composition formulated as a granulate having a bulk density of at least 600 g/L comprising: C12-C18 alkyl sulfate at about 9-15 wt %; alcohol ethoxylate at about 3-6 wt %; polyhydroxy alkyl fatty acid amide at about 1-5 wt %; zeolite (e.g., $NaAlSiO_4$) at about 10-20 wt %; layered disilicate (e.g., SK56 from Hoechst) at about 10-20 wt %; sodium carbonate at about 3-12 wt %; soluble silicate (e.g., $Na_2O\ 2SiO_2$) at 0-6 wt %; sodium citrate at about 4-8 wt %; sodium percarbonate at about 13-22 wt %; TAED at about 3-8 wt %; poly alpha-1,3-glucan ether up to about 2 wt %; other polymers (e.g., polycarboxylates and PVP) at about 0-5 wt %; optionally an enzyme(s) (calculated as pure enzyme protein) at about 0.0001-0.1 wt %; and minor ingredients (e.g., optical brightener, photobleach, perfume, suds suppressors) at about 0-5 wt %.

15) A detergent composition formulated as a granulate having a bulk density of at least 600 g/L comprising: C12-C18 alkyl sulfate at about 4-8 wt %; alcohol ethoxylate at about 11-15 wt %; soap at about 1-4 wt %; zeolite MAP or zeolite A at about 35-45 wt %; sodium carbonate at about 2-8 wt %; soluble silicate (e.g., $Na_2O\ 2SiO_2$) at 0-4 wt %; sodium percarbonate at about 13-22 wt %; TAED at about 1-8 wt %; poly alpha-1,3-glucan ether up to about 3 wt %;

other polymers (e.g., polycarboxylates and PVP) at about 0-3 wt %; optionally an enzyme(s) (calculated as pure enzyme protein) at about 0.0001-0.1 wt %; and minor ingredients (e.g., optical brightener, phosphonate, perfume) at about 0-3 wt %.

16) Detergent formulations as described in (1)-(15) above, but that contain a stabilized or encapsulated peracid, either as an additional component or as a substitute for an already specified bleach system(s).

17) Detergent compositions as described in (1), (3), (7), (9) and (12) above, but in which perborate is replaced by percarbonate.

18) Detergent compositions as described in (1), (3), (7), (9), (12), (14) and (15) above, but that additionally contain a manganese catalyst. A manganese catalyst, for example, is one of the compounds described by Hage et al. (1994, Nature 369:637-639), which is incorporated herein by reference.

19) Detergent compositions formulated as a non-aqueous detergent liquid comprising a liquid non-ionic surfactant (e.g., a linear alkoxylated primary alcohol), a builder system (e.g., phosphate), poly alpha-1,3-glucan ether, optionally an enzyme(s), and alkali. The detergent may also comprise an anionic surfactant and/or bleach system.

It is believed that numerous commercially available detergent formulations can be adapted to include a poly alpha-1,3-glucan ether compound. Examples include PUREX® ULTRAPACKS (Henkel), FINISH® QUANTUM (Reckitt Benckiser), CLOROX™ 2 PACKS (Clorox), OXICLEAN MAX FORCE POWER PAKS (Church & Dwight), TIDE® STAIN RELEASE, CASCADE® ACTIONPACS, and TIDE® PODS™ (Procter & Gamble).

Compositions disclosed herein can be in the form of an oral care composition. Examples of oral care compositions include dentifrices, toothpaste, mouth wash, mouth rinse, chewing gum, and edible strips that provide some form of oral care (e.g., treatment or prevention of cavities [dental caries], gingivitis, plaque, tartar, and/or periodontal disease). An oral care composition can also be for treating an "oral surface", which encompasses any soft or hard surface within the oral cavity including surfaces of the tongue, hard and soft palate, buccal mucosa, gums and dental surfaces. A "dental surface" herein is a surface of a natural tooth or a hard surface of artificial dentition including a crown, cap, filling, bridge, denture, or dental implant, for example.

One or more poly alpha-1,3-glucan and/or poly alpha-1,3-glucan ether compounds comprised in an oral care composition typically are provided therein as a thickening agent and/or dispersion agent, which may be useful to impart a desired consistency and/or mouth feel to the composition. An oral care composition herein can comprise about 0.01-15.0 wt % (e.g., ~0.1-10 wt % or ~0.1-5.0 wt %, ~0.1-2.0 wt %) of one or more poly alpha-1,3-glucan and/or poly alpha-1,3-glucan ether compounds disclosed herein (e.g., a quaternary ammonium poly alpha-1,3-glucan such as trimethylammonium hydroxypropyl poly alpha-1,3-glucan), for example. One or more other thickening agents and/or dispersion agents can also be provided in an oral care composition herein, such as a carboxyvinyl polymer, carrageenan (e.g., L-carrageenan), natural gum (e.g., karaya, xanthan, gum arabic, tragacanth), colloidal magnesium aluminum silicate, or colloidal silica, for example.

An oral care composition herein may be a toothpaste or other dentifrice, for example. Such compositions, as well as any other oral care composition herein, can additionally comprise, without limitation, one or more of an anticaries agent, antimicrobial or antibacterial agent, anticalculus or tartar control agent, surfactant, abrasive, pH-modifying agent, foam modulator, humectant, flavorant, sweetener, pigment/colorant, whitening agent, and/or other suitable components. Examples of oral care compositions to which one or more poly alpha-1,3-glucan ether compounds can be added are disclosed in U.S. Patent Appl. Publ. Nos. 2006/0134025, 2002/0022006 and 2008/0057007, which are incorporated herein by reference.

An anticaries agent herein can be an orally acceptable source of fluoride ions. Suitable sources of fluoride ions include fluoride, monofluorophosphate and fluorosilicate salts as well as amine fluorides, including olaflur (N'-octadecyltrimethylendiamine-N,N,N'-tris(2-ethanol)-dihydrofluoride), for example. An anticaries agent can be present in an amount providing a total of about 100-20000 ppm, about 200-5000 ppm, or about 500-2500 ppm, fluoride ions to the composition, for example. In oral care compositions in which sodium fluoride is the sole source of fluoride ions, an amount of about 0.01-5.0 wt %, about 0.05-1.0 wt %, or about 0.1-0.5 wt %, sodium fluoride can be present in the composition, for example.

An antimicrobial or antibacterial agent suitable for use in an oral care composition herein includes, for example, phenolic compounds (e.g., 4-allylcatechol; p-hydroxybenzoic acid esters such as benzylparaben, butylparaben, ethylparaben, methylparaben and propylparaben; 2-benzylphenol; butylated hydroxyanisole; butylated hydroxytoluene; capsaicin; carvacrol; creosol; eugenol; guaiacol; halogenated bisphenolics such as hexachlorophene and bromochlorophene; 4-hexylresorcinol; 8-hydroxyquinoline and salts thereof; salicylic acid esters such as menthyl salicylate, methyl salicylate and phenyl salicylate; phenol; pyrocatechol; salicylanilide; thymol; halogenated diphenylether compounds such as triclosan and triclosan monophosphate), copper (II) compounds (e.g., copper (II) chloride, fluoride, sulfate and hydroxide), zinc ion sources (e.g., zinc acetate, citrate, gluconate, glycinate, oxide, and sulfate), phthalic acid and salts thereof (e.g., magnesium monopotassium phthalate), hexetidine, octenidine, sanguinarine, benzalkonium chloride, domiphen bromide, alkylpyridinium chlorides (e.g. cetylpyridinium chloride, tetradecylpyridinium chloride, N-tetradecyl-4-ethylpyridinium chloride), iodine, sulfonamides, bisbiguanides (e.g., alexidine, chlorhexidine, chlorhexidine digluconate), piperidino derivatives (e.g., delmopinol, octapinol), *magnolia* extract, grapeseed extract, rosemary extract, menthol, geraniol, citral, eucalyptol, antibiotics (e.g., augmentin, amoxicillin, tetracycline, doxycycline, minocycline, metronidazole, neomycin, kanamycin, clindamycin), and/or any antibacterial agents disclosed in U.S. Pat. No. 5,776,435, which is incorporated herein by reference. One or more antimicrobial agents can optionally be present at about 0.01-10 wt % (e.g., 0.1-3 wt %), for example, in the disclosed oral care composition.

An anticalculus or tartar control agent suitable for use in an oral care composition herein includes, for example, phosphates and polyphosphates (e.g., pyrophosphates), polyaminopropanesulfonic acid (AMPS), zinc citrate trihydrate, polypeptides (e.g., polyaspartic and polyglutamic acids), polyolefin sulfonates, polyolefin phosphates, diphosphonates (e.g., azacycloalkane-2,2-diphosphonates such as azacycloheptane-2,2-diphosphonic acid), N-methyl azacyclopentane-2,3-diphosphonic acid, ethane-1-hydroxy-1,1-diphosphonic acid (EHDP), ethane-1-amino-1,1-diphosphonate, and/or phosphonoalkane carboxylic acids and salts thereof (e.g., their alkali metal and ammonium salts). Useful inorganic phosphate and polyphosphate salts include, for example, monobasic, dibasic and tribasic sodium phosphates, sodium tripolyphosphate, tetrapolyphosphate, mono-, di-, tri- and tetra-sodium pyrophosphates, disodium dihydrogen pyrophosphate, sodium trimetaphosphate, sodium hexametaphosphate, or any of these in which sodium is replaced by potassium or ammonium. Other useful anticalculus agents in certain embodiments include anionic polycarboxylate polymers (e.g., polymers or copolymers of acrylic acid, methacrylic, and maleic anhydride such as polyvinyl methyl ether/maleic anhydride copolymers). Still other useful anticalculus agents include sequestering agents such as hydroxycarboxylic acids (e.g., citric, fumaric, malic, glutaric and oxalic acids and salts thereof) and aminopolycarboxylic acids (e.g., EDTA). One or more anticalculus or tartar control agents can optionally be present at about 0.01-50 wt % (e.g., about 0.05-25 wt % or about 0.1-15 wt %), for example, in the disclosed oral care composition.

A surfactant suitable for use in an oral care composition herein may be anionic, non-ionic, or amphoteric, for example. Suitable anionic surfactants include, without limitation, water-soluble salts of $C_{8-20}$ alkyl sulfates, sulfonated monoglycerides of $C_{8-20}$ fatty acids, sarcosinates, and taurates. Examples of anionic surfactants include sodium lauryl sulfate, sodium coconut monoglyceride sulfonate, sodium lauryl sarcosinate, sodium lauryl isoethionate, sodium laureth carboxylate and sodium dodecyl benzenesulfonate. Suitable non-ionic surfactants include, without limitation, poloxamers, polyoxyethylene sorbitan esters, fatty alcohol ethoxylates, alkylphenol ethoxylates, tertiary amine oxides, tertiary phosphine oxides, and dialkyl sulfoxides. Suitable amphoteric surfactants include, without limitation, derivatives of $C_{8-20}$ aliphatic secondary and tertiary amines having an anionic group such as a carboxylate, sulfate, sulfonate, phosphate or phosphonate. An example of a suitable amphoteric surfactant is cocoamidopropyl betaine. One or more surfactants are optionally present in a total amount of about 0.01-10 wt % (e.g., about 0.05-5.0 wt % or about 0.1-2.0 wt %), for example, in the disclosed oral care composition.

An abrasive suitable for use in an oral care composition herein may include, for example, silica (e.g., silica gel, hydrated silica, precipitated silica), alumina, insoluble phosphates, calcium carbonate, and resinous abrasives (e.g., a urea-formaldehyde condensation product). Examples of insoluble phosphates useful as abrasives herein are orthophosphates, polymetaphosphates and pyrophosphates, and include dicalcium orthophosphate dihydrate, calcium pyrophosphate, beta-calcium pyrophosphate, tricalcium phosphate, calcium polymetaphosphate and insoluble sodium polymetaphosphate. One or more abrasives are optionally present in a total amount of about 5-70 wt % (e.g., about 10-56 wt % or about 15-30 wt %), for example, in the disclosed oral care composition. The average particle size of an abrasive in certain embodiments is about 0.1-30 microns (e.g., about 1-20 microns or about 5-15 microns).

An oral care composition in certain embodiments may comprise at least one pH-modifying agent. Such agents may be selected to acidify, make more basic, or buffer the pH of a composition to a pH range of about 2-10 (e.g., pH ranging from about 2-8, 3-9, 4-8, 5-7, 6-10, or 7-9). Examples of pH-modifying agents useful herein include, without limitation, carboxylic, phosphoric and sulfonic acids; acid salts (e.g., monosodium citrate, disodium citrate, monosodium malate); alkali metal hydroxides (e.g. sodium hydroxide, carbonates such as sodium carbonate, bicarbonates, sesquicarbonates); borates; silicates; phosphates (e.g., monosodium phosphate, trisodium phosphate, pyrophosphate salts); and imidazole.

A foam modulator suitable for use in an oral care composition herein may be a polyethylene glycol (PEG), for example. High molecular weight PEGs are suitable, including those having an average molecular weight of about 200000-7000000 (e.g., about 500000-5000000 or about 1000000-2500000), for example. One or more PEGs are optionally present in a total amount of about 0.1-10 wt % (e.g. about 0.2-5.0 wt % or about 0.25-2.0 wt %), for example, in the disclosed oral care composition.

An oral care composition in certain embodiments may comprise at least one humectant. A humectant in certain embodiments may be a polyhydric alcohol such as glycerin, sorbitol, xylitol, or a low molecular weight PEG. Most suitable humectants also may function as a sweetener herein. One or more humectants are optionally present in a total amount of about 1.0-70 wt % (e.g., about 1.0-50 wt %, about 2-25 wt %, or about 5-15 wt %), for example, in the disclosed oral care composition.

A natural or artificial sweetener may optionally be comprised in an oral care composition herein. Examples of suitable sweeteners include dextrose, sucrose, maltose, dextrin, invert sugar, mannose, xylose, ribose, fructose, levulose, galactose, corn syrup (e.g., high fructose corn syrup or corn syrup solids), partially hydrolyzed starch, hydrogenated starch hydrolysate, sorbitol, mannitol, xylitol, maltitol, isomalt, aspartame, neotame, saccharin and salts thereof, dipeptide-based intense sweeteners, and cyclamates. One or more sweeteners are optionally present in a total amount of about 0.005-5.0 wt %, for example, in the disclosed oral care composition.

A natural or artificial flavorant may optionally be comprised in an oral care composition herein. Examples of suitable flavorants include vanillin; sage; marjoram; parsley oil; spearmint oil; cinnamon oil; oil of wintergreen (methylsalicylate); peppermint oil; clove oil; bay oil; anise oil; *eucalyptus* oil; citrus oils; fruit oils; essences such as those derived from lemon, orange, lime, grapefruit, apricot, banana, grape, apple, strawberry, cherry, or pineapple; bean- and nut-derived flavors such as coffee, cocoa, cola, peanut, or almond; and adsorbed and encapsulated flavorants. Also encompassed within flavorants herein are ingredients that provide fragrance and/or other sensory effect in the mouth, including cooling or warming effects. Such ingredients include, without limitation, menthol, menthyl acetate, menthyl lactate, camphor, *eucalyptus* oil, eucalyptol, anethole, eugenol, *cassia*, oxanone, Irisone®, propenyl guaiethol, thymol, linalool, benzaldehyde, cinnamaldehyde, N-ethyl-p-menthan-3-carboxamine, N,2,3-trimethyl-2-isopropylbutanamide, 3-(1-menthoxy)-propane-1,2-diol, cinnamaldehyde glycerol acetal (CGA), and menthone glycerol acetal (MGA). One or more flavorants are optionally present in a total amount of about 0.01-5.0 wt % (e.g., about 0.1-2.5 wt %), for example, in the disclosed oral care composition.

An oral care composition in certain embodiments may comprise at least one bicarbonate salt. Any orally acceptable bicarbonate can be used, including alkali metal bicarbonates such as sodium or potassium bicarbonate, and ammonium bicarbonate, for example. One or more bicarbonate salts are optionally present in a total amount of about 0.1-50 wt % (e.g., about 1-20 wt %), for example, in the disclosed oral care composition.

An oral care composition in certain embodiments may comprise at least one whitening agent and/or colorant. A suitable whitening agent is a peroxide compound such as any of those disclosed in U.S. Pat. No. 8,540,971, which is incorporated herein by reference. Suitable colorants herein include pigments, dyes, lakes and agents imparting a particular luster or reflectivity such as pearling agents, for example. Specific examples of colorants useful herein include talc; mica; magnesium carbonate; calcium carbonate; magnesium silicate; magnesium aluminum silicate; silica; titanium dioxide; zinc oxide; red, yellow, brown and black iron oxides; ferric ammonium ferrocyanide; manganese violet; ultramarine; titaniated mica; and bismuth oxychloride. One or more colorants are optionally present in a total amount of about 0.001-20 wt % (e.g., about 0.01-10 wt % or about 0.1-5.0 wt %), for example, in the disclosed oral care composition.

Additional components that can optionally be included in an oral composition herein include one or more enzymes (above), vitamins, and anti-adhesion agents, for example. Examples of vitamins useful herein include vitamin C, vitamin E, vitamin B5, and folic acid. Examples of suitable anti-adhesion agents include solbrol, ficin, and quorum-sensing inhibitors.

The disclosed invention also concerns a method for increasing the viscosity of an aqueous composition. This method comprises contacting one or more poly alpha-1,3-glucan ether compounds disclosed herein with the aqueous composition. This step results in increasing the viscosity of the aqueous composition. The poly alpha-1,3-glucan ether compound(s) used in this method can be represented by the structure:

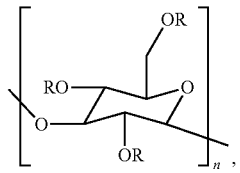

Regarding the formula of this structure, n can be at least 6, and each R can independently be an H or a positively charged organic group. Furthermore, the poly alpha-1,3-glucan ether compound has a degree of substitution of about 0.05 to about 3.0. Any hydrocolloid and aqueous solution disclosed herein can be produced using this method.

An aqueous composition herein can be water (e.g., de-ionized water), an aqueous solution, or a hydrocolloid, for example. The viscosity of an aqueous composition before the contacting step, measured at about 20-25° C., can be about 0-10000 cPs (or any integer between 0-10000 cPs), for example. Since the aqueous composition can be a hydrocolloid or the like in certain embodiments, it should be apparent that the method can be used to increase the viscosity of aqueous compositions that are already viscous.

Contacting a poly alpha-1,3-glucan ether compound disclosed herein with an aqueous composition increases the viscosity of the aqueous composition in certain embodiments. This increase in viscosity can be an increase of at least about 1%, 10%, 100%, 1000%, 100000%, or 1000000% (or any integer between 1% and 1000000%), for example, compared to the viscosity of the aqueous composition before the contacting step. It should be apparent that very large percent increases in viscosity can be obtained with the disclosed method when the aqueous composition has little to no viscosity before the contacting step.

Contacting a poly alpha-1,3-glucan ether compound disclosed herein with an aqueous composition increases the shear thinning behavior or the shear thickening behavior of the aqueous composition in certain embodiments. Thus, a poly alpha-1,3-glucan ether compound rheologically modifies the aqueous composition in these embodiments. The increase in shear thinning or shear thickening behavior can be an increase of at least about 1%, 10%, 100%, 1000%, 100000%, or 1000000% (or any integer between 1% and 1000000%), for example, compared to the shear thinning or shear thickening behavior of the aqueous composition before the contacting step. It should be apparent that very large percent increases in rheologic modification can be obtained with the disclosed method when the aqueous composition has little to no rheologic behavior before the contacting step.

The contacting step can be performed by mixing or dissolving a poly alpha-1,3-glucan ether compound(s) disclosed herein in the aqueous composition by any means known in the art. For example, mixing or dissolving can be performed manually or with a machine (e.g., industrial mixer or blender, orbital shaker, stir plate, homogenizer, sonicator, bead mill). Mixing or dissolving can comprise a homogenization step in certain embodiments. Homogenization (as well as any other type of mixing) can be performed for about 5 to 60, 5 to 30, 10 to 60, 10 to 30, 5 to 15, or 10 to 15 seconds (or any integer between 5 and 60 seconds), or longer periods of time as necessary to mix a poly alpha-1,3-glucan ether compound with the aqueous composition. A homogenizer can be used at about 5000 to 30000 rpm, 10000 to 30000 rpm, 15000 to 30000 rpm, 15000 to 25000 rpm, or 20000 rpm (or any integer between 5000 and 30000 rpm), for example. Hydrocolloids and aqueous solutions disclosed herein prepared using a homogenization step can be termed as homogenized hydrocolloids and aqueous solutions.

After a poly alpha-1,3-glucan ether compound is mixed with or dissolved into an aqueous composition, the resulting aqueous composition may be filtered, or may not be filtered. For example, an aqueous composition prepared with a homogenization step may or may not be filtered.

Certain embodiments of the above method can be used to prepare an aqueous composition disclosed herein, such as a household product (e.g., laundry detergent, fabric softener, dishwasher detergent), personal care product (e.g., a water-containing dentifrice such as toothpaste), or industrial product.

The disclosed invention also concerns a method of treating a material. This method comprises contacting a material with an aqueous composition comprising at least one poly alpha-1,3-glucan ether compound disclosed herein. A poly alpha-1,3-glucan ether compound(s) used in this method is represented by the structure:

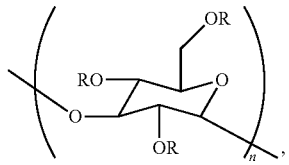

Regarding the formula of this structure, n can be at least 6, and each R can independently be an H or a positively charged organic group. Furthermore, the poly alpha-1,3-glucan ether compound has a degree of substitution of about 0.05 to about 3.0.

A material contacted with an aqueous composition in a contacting method herein can comprise a fabric in certain embodiments. A fabric herein can comprise natural fibers, synthetic fibers, semi-synthetic fibers, or any combination thereof. A semi-synthetic fiber herein is produced using naturally occurring material that has been chemically derivatized, an example of which is rayon. Non-limiting examples of fabric types herein include fabrics made of (i) cellulosic fibers such as cotton (e.g., broadcloth, canvas, chambray, chenille, chintz, corduroy, cretonne, damask, denim, flannel, gingham, jacquard, knit, matelassé, oxford, percale, poplin, plisse, sateen, seersucker, sheers, terry cloth, twill, velvet), rayon (e.g., viscose, modal, lyocell), linen, and Tencel®; (ii) proteinaceous fibers such as silk, wool and related mammalian fibers; (iii) synthetic fibers such as polyester, acrylic, nylon, and the like; (iv) long vegetable fibers from jute, flax, ramie, coir, kapok, sisal, henequen, abaca, hemp and sunn; and (v) any combination of a fabric of (i)-(iv). Fabric comprising a combination of fiber types (e.g., natural and synthetic) include those with both a cotton fiber and polyester, for example. Materials/articles containing one or more fabrics herein include, for example, clothing, curtains, drapes, upholstery, carpeting, bed linens, bath linens, tablecloths, sleeping bags, tents, car interiors, etc. Other materials comprising natural and/or synthetic fibers include, for example, non-woven fabrics, paddings, paper, and foams.

An aqueous composition that is contacted with a fabric can be, for example, a fabric care composition (e.g., laundry detergent, fabric softener). Thus, a treatment method in certain embodiments can be considered a fabric care method or laundry method if employing a fabric care composition therein. A fabric care composition herein can effect one or more of the following fabric care benefits (i.e., surface substantive effects): wrinkle removal, wrinkle reduction, wrinkle resistance, fabric wear reduction, fabric wear resistance, fabric pilling reduction, fabric color maintenance, fabric color fading reduction, fabric color restoration, fabric soiling reduction, fabric soil release, fabric shape retention, fabric smoothness enhancement, anti-redeposition of soil on fabric, anti-greying of laundry, improved fabric hand/handle, and/or fabric shrinkage reduction.

Examples of conditions (e.g., time, temperature, wash/rinse volumes) for conducting a fabric care method or laundry method herein are disclosed in WO1997/003161 and U.S. Pat. Nos. 4,794,661, 4,580,421 and 5,945,394, which are incorporated herein by reference. In other examples, a material comprising fabric can be contacted with an aqueous composition herein: (i) for at least about 5, 10, 20, 30, 40, 50, 60, 70, 80, 90, 100, 110, or 120 minutes; (ii) at a temperature of at least about 10, 15, 20, 25, 30, 35, 40, 45, 50, 55, 60, 65, 70, 75, 80, 85, 90, or 95° C. (e.g., for laundry wash or rinse: a "cold" temperature of about 15-30° C., a "warm" temperature of about 30-50° C., a "hot" temperature of about 50-95° C.); (iii) at a pH of about 2, 3, 4, 5, 6, 7, 8, 9, 10, 11, or 12 (e.g., pH range of about 2-12, or about 3-11); (iv) at a salt (e.g., NaCl) concentration of at least about 0.5, 1.0, 1.5, 2.0, 2.5, 3.0, 3.5, or 4.0 wt %; or any combination of (i)-(iv).

The contacting step in a fabric care method or laundry method can comprise any of washing, soaking, and/or rinsing steps, for example. Contacting a material or fabric in still further embodiments can be performed by any means known in the art, such as dissolving, mixing, shaking, spraying, treating, immersing, flushing, pouring on or in, combining, painting, coating, applying, affixing to, and/or communicating an effective amount of a poly alpha-1,3-glucan ether compound herein with the fabric or material. In still further embodiments, contacting may be used to treat a fabric to provide a surface substantive effect. As used herein, the term "fabric hand" or "handle" refers to a person's tactile sensory response towards fabric which may be physical, physiological, psychological, social or any combination thereof. In one embodiment, the fabric hand may be measured using a PhabrOmeter® System for measuring relative hand value (available from Nu Cybertek, Inc. Davis, Calif.) (American Association of Textile Chemists and Colorists (AATCC test method "202-2012, Relative Hand Value of Textiles: Instrumental Method")).

In certain embodiments of treating a material comprising fabric, a poly alpha-1,3-glucan ether compound component(s) of the aqueous composition adsorbs to the fabric. This feature is believed to render poly alpha-1,3-glucan ether compounds (e.g., quaternary ammonium poly alpha-1,3-glucan ether compounds such as trimethylammonium hydroxypropyl poly alpha-1,3-glucan) useful as anti-redeposition agents and/or anti-greying agents in fabric care compositions disclosed herein (in addition to their viscosity-modifying effect). An anti-redeposition agent or anti-greying agent herein helps keep soil from redepositing onto clothing in wash water after the soil has been removed. It is further contemplated that adsorption of one or more poly alpha-1,3-glucan ether compounds herein to a fabric enhances mechanical properties of the fabric.

The below Examples demonstrate that poly alpha-1,3-glucan ether compounds such as quaternary ammonium poly alpha-1,3-glucan (e.g., trimethylammonium hydroxypropyl poly alpha-1,3-glucan) can adsorb to both natural (cotton, cretonne) and synthetic (polyester) fabrics, as well as a blend thereof (polyester/cretonne). This result is notable given that carboxymethyl cellulose (CMC) does not absorb to, or only poorly adsorbs to, polyester and polyester/cotton blends (see European Pat. Appl. Publ. No. EP0035478, for example). Thus, in certain embodiments of a treatment method herein, a cationic poly alpha-1,3-glucan ether compound (e.g., quaternary ammonium poly alpha-1,3-glucan such as trimethylammonium hydroxypropyl poly alpha-1,3-glucan) adsorbs to material comprising natural fiber (e.g. cotton) and/or synthetic fiber (e.g., polyester). Such adsorption may optionally be under conditions of about 1-2 wt % salt (e.g., NaCl), and/or a pH of about 3.0, 3.5, 4.0, 4.5, 5.0, 5.5, 6.0, 6.5, 7.0, 7.5, 8.0, 8.5, 9.0, or 9.5, for example.

Adsorption of a poly alpha-1,3-glucan ether compound to a fabric herein can be measured following the methodology disclosed in the below Examples, for example. Alternatively, adsorption can be measured using a colorimetric technique (e.g., Dubois et al., 1956, *Anal. Chem.* 28:350-356; Zemljič et al., 2006, *Lenzinger Berichte* 85:68-76; both incorporated herein by reference) or any other method known in the art.

Other materials that can be contacted in the above treatment method include surfaces that can be treated with a dish detergent (e.g., automatic dishwashing detergent or hand dish detergent). Examples of such materials include surfaces of dishes, glasses, pots, pans, baking dishes, utensils and flatware made from ceramic material, china, metal, glass, plastic (e.g., polyethylene, polypropylene, polystyrene, etc.) and wood (collectively referred to herein as "tableware"). Thus, the treatment method in certain embodiments can be considered a dishwashing method or tableware washing method, for example. Examples of conditions (e.g., time, temperature, wash volume) for conducting a dishwashing or tableware washing method herein are disclosed in U.S. Pat. No. 8,575,083, which is incorporated herein by reference. In other examples, a tableware article can be contacted with an aqueous composition herein under a suitable set of conditions such as any of those disclosed above with regard to contacting a fabric-comprising material.

Other materials that can be contacted in the above treatment method include oral surfaces such as any soft or hard surface within the oral cavity including surfaces of the tongue, hard and soft palate, buccal mucosa, gums and dental surfaces (e.g., natural tooth or a hard surface of artificial dentition such as a crown, cap, filling, bridge, denture, or dental implant). Thus, a treatment method in certain embodiments can be considered an oral care method or dental care method, for example. Conditions (e.g., time, temperature) for contacting an oral surface with an aqueous composition herein should be suitable for the intended purpose of making such contact. Other surfaces that can be contacted in a treatment method also include a surface of the integumentary system such as skin, hair or nails.

Thus, certain embodiments of the disclosed invention concern material (e.g., fabric) that comprises a poly alpha-1,3-glucan ether compound herein. Such material can be produced following a material treatment method as disclosed, for example. A material may comprise a glucan ether compound in certain embodiments if the compound is adsorbed to, or otherwise in contact with, the surface of the material.

Certain embodiments of a method of treating a material herein further comprise a drying step, in which a material is dried after being contacted with the aqueous composition. A drying step can be performed directly after the contacting step, or following one or more additional steps that might follow the contacting step (e.g., drying of a fabric after being rinsed, in water for example, following a wash in an aqueous composition herein). Drying can be performed by any of several means known in the art, such as air drying (e.g., ~20-25° C.), or at a temperature of at least about 30, 40, 50, 60, 70, 80, 90, 100, 120, 140, 160, 170, 175, 180, or 200° C., for example. A material that has been dried herein typically has less than 3, 2, 1, 0.5, or 0.1 wt % water comprised therein. Fabric is a preferred material for conducting an optional drying step.

An aqueous composition used in a treatment method herein can be any aqueous composition disclosed herein, such as in the above embodiments or in the below Examples. Thus, the poly alpha-1,3-glucan ether component(s) of an aqueous composition can be any as disclosed herein. Examples of aqueous compositions include detergents (e.g., laundry detergent or dish detergent) and water-containing dentifrices such as toothpaste.

The disclosed invention also concerns a method for producing a poly alpha-1,3-glucan ether compound. This method comprises: contacting poly alpha-1,3-glucan in a reaction under alkaline conditions with at least one etherification agent comprising a positively charged organic group, wherein the positively charged organic group is etherified to the poly alpha-1,3-glucan thereby producing a poly alpha-1,3-glucan ether compound represented by the structure:

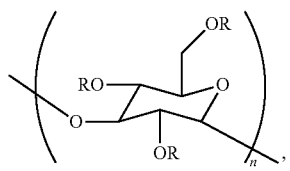

wherein
(i) n is at least 6,
(ii) each R is independently an H or the positively charged organic group, and
(iii) the compound has a degree of substitution of about 0.05 to about 3.0.

A poly alpha-1,3-glucan ether produced by this method can optionally be isolated. This method can be considered to comprise an etherification reaction.

Poly alpha-1,3-glucan is contacted in a reaction under alkaline conditions with at least one etherification agent comprising a positively charged organic group. This step can be performed, for example, by first preparing alkaline conditions by contacting poly alpha-1,3-glucan with a solvent and one or more alkali hydroxides to provide a solution or mixture. The alkaline conditions of the reaction can thus comprise an alkali hydroxide solution. The pH of the alkaline conditions can be at least about 11.0, 11.2, 11.4, 11.6, 11.8, 12.0, 12.2, 12.4, 12.6, 12.8, or 13.0.

Various alkali hydroxides can be used, such as sodium hydroxide, potassium hydroxide, calcium hydroxide, lithium hydroxide, and/or tetraethylammonium hydroxide. The concentration of alkali hydroxide in a preparation with poly alpha-1,3-glucan and a solvent can be from about 1-70 wt %, 5-50 wt %, 10-50 wt %, 10-40 wt %, or 10-30 wt % (or any integer between 1 and 70 wt %). Alternatively, the concentration of alkali hydroxide such as sodium hydroxide can be at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 wt %. An alkali hydroxide used to prepare alkaline conditions may be in a completely aqueous solution or an aqueous solution comprising one or more water-soluble organic solvents such as ethanol or isopropanol. Alternatively, an alkali hydroxide can be added as a solid to provide alkaline conditions.

Various organic solvents that can optionally be included when preparing the reaction include alcohols, acetone, dioxane, isopropanol and toluene, for example; none of these solvents dissolve poly alpha-1,3-glucan. Toluene or isopropanol can be used in certain embodiments. An organic solvent can be added before or after addition of alkali hydroxide. The concentration of an organic solvent (e.g., isopropanol or toluene) in a preparation comprising poly alpha-1,3-glucan and an alkali hydroxide can be at least about 10, 15, 20, 25, 30, 35, 40, 45, 50, 55, 60, 65, 70, 75, 80, 85, or 90 wt % (or any integer between 10 and 90 wt %).

Alternatively, solvents that can dissolve poly alpha-1,3-glucan can be used when preparing the reaction. These solvents include, but are not limited to, lithium chloride (LiCl)/N,N-dimethyl-acetamide (DMAc), SO$_2$/diethylamine (DEA)/dimethyl sulfoxide (DMSO), LiCl/1,3-dimethy-2-imidazolidinone (DMI) N,N-dimethylformamide (DMF)/N$_2$O$_4$, DMSO/tetrabutyl-ammonium fluoride trihydrate (TBAF), N-methylmorpholine-N-oxide (NMMO), Ni(tren)(OH)$_2$ [tren¼tris(2-aminoethyl)amine]aqueous solutions and melts of LiClO$_4$.3H$_2$O, NaOH/urea aqueous solutions, aqueous sodium hydroxide, aqueous potassium hydroxide, formic acid, and ionic liquids.

Poly alpha-1,3-glucan can be contacted with a solvent and one or more alkali hydroxides by mixing. Such mixing can be performed during or after adding these components with each other. Mixing can be performed by manual mixing, mixing using an overhead mixer, using a magnetic stir bar, or shaking, for example. In certain embodiments, poly alpha-1,3-glucan can first be mixed in water or an aqueous solution before it is mixed with a solvent and/or alkali hydroxide.

After contacting poly alpha-1,3-glucan, solvent, and one or more alkali hydroxides with each other, the resulting composition can optionally be maintained at ambient temperature for up to 14 days. The term "ambient temperature" as used herein refers to a temperature between about 15-30° C. or 20-25° C. (or any integer between 15 and 30° C.).

Alternatively, the composition can be heated with or without reflux at a temperature from about 30° C. to about 150° C. (or any integer between 30 and 150° C.) for up to about 48 hours. The composition in certain embodiments can be heated at about 55° C. for about 30 minutes or 60 minutes. Thus, a composition obtained from mixing a poly alpha-1,3-glucan, solvent, and one or more alkali hydroxides with each other can be heated at about 50, 51, 52, 53, 54, 55, 56, 57, 58, 59, or 60° C. for about 30-90 minutes.

After contacting poly alpha-1,3-glucan, solvent, and one or more alkali hydroxides with each other, the resulting composition can optionally be filtered (with or without applying a temperature treatment step). Such filtration can be performed using a funnel, centrifuge, press filter, or any other method and/or equipment known in the art that allows removal of liquids from solids. Though filtration would remove much of the alkali hydroxide, the filtered poly alpha-1,3-glucan would remain alkaline (i.e., mercerized poly alpha-1,3-glucan), thereby providing alkaline conditions.

An etherification agent comprising a positively charged organic group can be contacted with poly alpha-1,3-glucan in a reaction under alkaline conditions in a method herein of producing poly alpha-1,3-glucan ether compounds. For example, an etherification agent can be added to a composition prepared by contacting poly alpha-1,3-glucan, solvent, and one or more alkali hydroxides with each other as described above. Alternatively, an etherification agent can be included when preparing the alkaline conditions (e.g., an etherification agent can be mixed with poly alpha-1,3-glucan and solvent before mixing with alkali hydroxide).

An etherification agent herein refers to an agent that can be used to etherify one or more hydroxyl groups of the glucose units of poly alpha-1,3-glucan with a positively charged organic group as defined above. One or more etherification agents may be used in the reaction.

An etherification agent may be one that can etherify poly alpha-1,3-glucan with a positively charged organic group, where the carbon chain of the positively charged organic group only has a substitution with a positively charged group (e.g., substituted ammonium group such as trimethylammonium). Examples of such etherification agents include dialkyl sulfates, dialkyl carbonates, alkyl halides (e.g., alkyl chloride), iodoalkanes, alkyl triflates (alkyl trifluoromethanesulfonates) and alkyl fluorosulfonates, where the alkyl group(s) of each of these agents has one or more substitutions with a positively charged group (e.g., substituted ammonium group such as trimethylammonium). Other examples of such etherification agents include dimethyl sulfate, dimethyl carbonate, methyl chloride, iodomethane, methyl triflate and methyl fluorosulfonate, where the methyl group(s) of each of these agents has a substitution with a positively charged group (e.g., substituted ammonium group such as trimethylammonium). Other examples of such etherification agents include diethyl sulfate, diethyl carbonate, ethyl chloride, iodoethane, ethyl triflate and ethyl fluorosulfonate, where the ethyl group(s) of each of these agents has a substitution with a positively charged group (e.g., substituted ammonium group such as trimethylammonium). Other examples of such etherification agents include dipropyl sulfate, dipropyl carbonate, propyl chloride, iodopropane, propyl triflate and propyl fluorosulfonate, where the propyl group(s) of each of these agents has one or more substitutions with a positively charged group (e.g., substituted ammonium group such as trimethylammonium). Other examples of such etherification agents include dibutyl sulfate, dibutyl carbonate, butyl chloride, iodobutane and butyl triflate, where the butyl group(s) of each of these agents has one or more substitutions with a positively charged group (e.g., substituted ammonium group such as trimethylammonium).

An etherification agent may be one that can etherify poly alpha-1,3-glucan with a positively charged organic group, where the carbon chain of the positively charged organic group has a substitution (e.g., hydroxyl group) in addition to a substitution with a positively charged group (e.g., substituted ammonium group such as trimethylammonium). Examples of such etherification agents include hydroxyalkyl halides (e.g., hydroxyalkyl chloride) such as hydroxypropyl halide and hydroxybutyl halide, where a terminal carbon of each of these agents has a substitution with a positively charged group (e.g., substituted ammonium group such as trimethylammonium); an example is 3-chloro-2-hydroxypropyl-trimethylammonium. Other examples of such etherification agents include alkylene oxides such as propylene oxide (e.g., 1,2-propylene oxide) and butylene oxide (e.g., 1,2-butylene oxide; 2,3-butylene oxide), where a terminal carbon of each of these agents has a substitution with a positively charged group (e.g., substituted ammonium group such as trimethylammonium).

A substituted ammonium group comprised in any of the foregoing etherification agent examples can be a primary, secondary, tertiary, or quaternary ammonium group. Examples of secondary, tertiary and quaternary ammonium groups are represented in structure I, where $R_2$, $R_3$ and $R_4$ each independently represent a hydrogen atom or an alkyl group such as a methyl, ethyl, propyl, or butyl group.

Etherification agents herein typically can be provided as a fluoride, chloride, bromide, or iodide salt (where each of the foregoing halides serve as an anion).

Any of the etherification agents disclosed herein may be combined to produce poly alpha-1,3-glucan ether compounds with two or more different positively charged organic groups. Such two or more etherification agents may be used in the reaction at the same time, or may be used sequentially in the reaction. When used sequentially, any of the temperature-treatment (e.g., heating) steps disclosed below may optionally be used between each addition. One may choose sequential introduction of etherification agents in order to control the desired DoS of each positively charged organic group. In general, a particular etherification agent would be used first if the positively charged organic group it forms in the ether product is desired at a higher DoS compared to the DoS of another positively charged organic group to be added.

The amount of etherification agent to be contacted with poly alpha-1,3-glucan in a reaction under alkaline conditions can be determined based on the degree of substitution required in the poly alpha-1,3-glucan ether compound being produced. The amount of ether substitution groups on each monomeric unit in poly alpha-1,3-glucan ether compounds produced herein can be determined using nuclear magnetic resonance (NMR) spectroscopy. The molar substitution (MS) value for poly alpha-1,3-glucan has no upper limit. In general, an etherification agent can be used in a quantity of at least about 0.05 mole per mole of poly alpha-1,3-glucan. There is no upper limit to the quantity of etherification agent that can be used.

Reactions for producing poly alpha-1,3-glucan ether compounds herein can optionally be carried out in a pressure vessel such as a Parr reactor, an autoclave, a shaker tube or any other pressure vessel well known in the art. A shaker tube is used to perform the reaction in certain embodiments.

A reaction herein can optionally be heated following the step of contacting poly alpha-1,3-glucan with an etherification agent under alkaline conditions. The reaction temperatures and time of applying such temperatures can be varied within wide limits. For example, a reaction can optionally be maintained at ambient temperature for up to 14 days. Alternatively, a reaction can be heated, with or without reflux, between about 25° C. to about 200° C. (or any integer between 25 and 200° C.). Reaction time can be varied correspondingly: more time at a low temperature and less time at a high temperature.

In certain embodiments of producing quaternary ammonium poly alpha-1,3-glucan ether (e.g., trimethylammonium hydroxypropyl poly alpha-1,3-glucan), a reaction can be heated to about 55° C. for about 1.5 hours. Thus, a reaction for preparing a quaternary ammonium poly alpha-1,3-glucan ether such as trimethylammonium hydroxypropyl poly alpha-1,3-glucan can optionally be heated to about 50-60° C. for about 1-2 hours, for example. Such a reaction may comprise 3-chloro-2-hydroxypropyl-trimethylammonium as an etherification agent.

Optionally, a reaction herein can be maintained under an inert gas, with or without heating. As used herein, the term "inert gas" refers to a gas which does not undergo chemical reactions under a set of given conditions, such as those disclosed for preparing a reaction herein.

All of the components of the reactions disclosed herein can be mixed together at the same time and brought to the desired reaction temperature, whereupon the temperature is maintained with or without stirring until the desired poly alpha-1,3-glucan ether compound is formed. Alternatively, the mixed components can be left at ambient temperature as described above.

Following etherification, the pH of a reaction can be neutralized. Neutralization of a reaction can be performed using one or more acids. The term "neutral pH" as used herein, refers to a pH that is neither substantially acidic or basic (e.g., a pH of about 6-8, or about 6.0, 6.2, 6.4, 6.6, 6.8, 7.0, 7.2, 7.4, 7.6, 7.8, or 8.0). Various acids that can be used for this purpose include, but are not limited to, sulfuric, acetic, hydrochloric, nitric, any mineral (inorganic) acid, any organic acid, or any combination of these acids.

A poly alpha-1,3-glucan ether compound produced in a reaction herein can optionally be washed one or more times with a liquid that does not readily dissolve the compound. For example, poly alpha-1,3-glucan ether can be washed with alcohol, acetone, aromatics, or any combination of these, depending on the solubility of the ether compound therein (where lack of solubility is desirable for washing). A poly alpha-1,3-glucan ether product can be washed one or more times with an aqueous solution containing methanol or ethanol, for example. For example, 70-95 wt % ethanol can be used to wash the product. A poly alpha-1,3-glucan ether product can be washed with a methanol:acetone (e.g., 60:40) solution in another embodiment.

A poly alpha-1,3-glucan ether produced in the disclosed reaction can be isolated. This step can be performed before or after neutralization and/or washing steps using a funnel, centrifuge, press filter, or any other method or equipment known in the art that allows removal of liquids from solids. For example, a Buchner funnel may be used to isolate a poly alpha-1,3-glucan ether product. An isolated poly alpha-1,3-glucan ether product can be dried using any method known in the art, such as vacuum drying, air drying, or freeze drying.

Any of the above etherification reactions can be repeated using a poly alpha-1,3-glucan ether product as the starting material for further modification. This approach may be suitable for increasing the DoS of a positively charged organic group, and/or adding one or more different positively charged organic groups to the ether product. Also, this approach may be suitable for adding one or more organic groups that are not positively charged, such as an alkyl group (e.g., methyl, ethyl, propyl, butyl) and/or a hydroxyalkyl group (e.g., hydroxyethyl, hydroxypropyl, hydroxybutyl). Any of the above etherification agents, but without the substitution with a positively charged group, can be used for this purpose.

The structure, molecular weight and degree of substitution of a poly alpha-1,3-glucan ether product can be confirmed using various physiochemical analyses known in the art such as NMR spectroscopy and size exclusion chromatography (SEC).

The percentage of glycosidic linkages between the glucose monomer units of poly alpha-1,3-glucan used to prepare poly alpha-1,3-glucan ether compounds herein that are alpha-1,3 is at least about 50%, 60%, 70%, 80%, 90%, 95%, 96%, 97%, 98%, 99%, or 100% (or any integer value between 50% and 100%). In such embodiments, accordingly, poly alpha-1,3-glucan has less than about 50%, 40%, 30%, 20%, 10%, 5%, 4%, 3%, 2%, 1%, or 0% (or any integer value between 0% and 50%) of glycosidic linkages that are not alpha-1,3.

Poly alpha-1,3-glucan used to prepare poly alpha-1,3-glucan ether compounds herein is preferably linear/unbranched. In certain embodiments, poly alpha-1,3-glucan has no branch points or less than about 10%, 9%, 8%, 7%, 6%, 5%, 4%, 3%, 2%, or 1% branch points as a percent of the glycosidic linkages in the polymer. Examples of branch points include alpha-1,6 branch points.

The $M_n$ or $M_w$ of poly alpha-1,3-glucan used to prepare poly alpha-1,3-glucan ether compounds herein may be at least about 1000 to about 600000. Alternatively still, $M_n$ or $M_w$ can be at least about 2000, 3000, 4000, 5000, 6000, 7000, 8000, 9000, 10000, 15000, 20000, 25000, 30000, 35000, 40000, 45000, 50000, 75000, 100000, 150000, 200000, 250000, 300000, 350000, 400000, 450000, 500000, 550000, or 600000 (or any integer between 2000 and 600000), for example.

Poly alpha-1,3-glucan used for preparing poly alpha-1,3-glucan ether compounds herein can be enzymatically produced from sucrose using one or more glucosyltransferase (gtf) enzymes. The poly alpha-1,3-glucan product of this enzymatic reaction can be purified before using it to prepare an ether using the disclosed process. Alternatively, a poly alpha-1,3-glucan product of a gtf reaction can be used with little or no processing for preparing poly alpha-1,3-glucan ether compounds.

A poly alpha-1,3-glucan slurry can be used directly in any of the above processes for producing a poly alpha-1,3-glucan ether compound disclosed herein. As used herein, a "poly alpha-1,3-glucan slurry" refers to a mixture comprising the components of a gtf enzymatic reaction. A gtf enzymatic reaction can include, in addition to poly alpha-1,3-glucan itself, various components such as sucrose, one or more gtf enzymes, glucose, fructose, leucrose, buffer, FermaSure®, soluble oligosaccharides, oligosaccharide primers, bacterial enzyme extract components, borates, sodium hydroxide, hydrochloric acid, cell lysate, proteins and/or nucleic acids. Minimally, the components of a gtf enzymatic reaction can include, in addition to poly alpha-1,3-glucan itself, sucrose, one or more gtf enzymes, glucose and fructose, for example. In another example, the components of a gtf enzymatic reaction can include, in addition to poly alpha-1,3-glucan itself, sucrose, one or more gtf enzymes, glucose, fructose, leucrose and soluble oligosaccharides (and optionally bacterial enzyme extract components). It should be apparent that poly alpha-1,3-glucan, when in a slurry as disclosed herein, has not been purified or washed. It should also be apparent that a slurry represents a gtf enzymatic reaction that is complete or for which an observable amount of poly alpha-1,3-glucan has been produced, which forms a solid since it is insoluble in the aqueous reaction milieu (has pH of 5-7, for example). A poly alpha-1,3-glucan slurry can be prepared by setting up a gtf reaction as disclosed in U.S. Pat. No. 7,000,000 or U.S. Patent Appl. Publ. Nos. 2013/0244288 and 2013/0244287, for example, all of which are incorporated herein by reference. A poly alpha-1,3-glucan slurry can be entered into a reaction for producing any ether compound herein, such as a quaternary ammonium poly alpha-1,3-glucan ether (e.g., trimethylammonium hydroxypropyl poly alpha-1,3-glucan).

Alternatively, a wet cake of poly alpha-1,3-glucan can be used directly in any of the above processes for producing a poly alpha-1,3-glucan ether compound disclosed herein. A "wet cake of poly alpha-1,3-glucan" as used herein refers to poly alpha-1,3-glucan that has been separated (e.g., filtered) from a slurry and washed with water or an aqueous solution. A wet cake can be washed at least 1, 2, 3, 4, 5, or more times, for example. The poly alpha-1,3-glucan is not dried when preparing a wet cake. A wet cake is termed as "wet" given the retention of water by the washed poly alpha-1,3-glucan.

A wet cake of poly alpha-1,3-glucan can be prepared using any device known in the art for separating solids from liquids, such as a filter or centrifuge. For example, poly alpha-1,3-glucan solids in a slurry can be collected on a Buchner funnel using a mesh screen over filter paper. Filtered wet cake can be resuspended in water (e.g., deionized water) and filtered one or more times to remove soluble components of the slurry such as sucrose, fructose and leucrose. As another example for preparing a wet cake, poly alpha-1,3-glucan solids from a slurry can be collected as a pellet via centrifugation, resuspended in water (e.g., deionized water), and re-pelleted and resuspended one or more additional times. A poly alpha-1,3-glucan wet cake can be entered into a reaction for producing any ether compound herein, such as a quaternary ammonium poly alpha-1,3-glucan ether (e.g., trimethylammonium hydroxypropyl poly alpha-1,3-glucan).

Poly alpha-1,3-glucan ether compounds disclosed herein may be crosslinked using any means known in the art. Such crosslinkage may be between the same poly alpha-1,3-glucan ether compounds, or between two or more different poly alpha-1,3-glucan ether compounds. Also, crosslinkage may be intermolecular and/or intramolecular.

A crosslinked poly alpha-1,3-glucan ether compound can be prepared as follows, for example. One or more poly alpha-1,3-glucan ether compounds can be dissolved in water or an aqueous solution to prepare a 0.2, 0.5, 1, 2, 3, 4, 5, 6, 7, 8, 9, or 10 wt % solution of the ether compound(s). Poly alpha-1,3-glucan ether compound(s) can be dissolved or mixed using any process known in the art, such as by increasing temperature, manual mixing, and/or homogenization (as described above).

A crosslinking agent is next dissolved in the poly alpha-1,3-glucan ether solution or mixture. The concentration of the crosslinking agent in the resulting solution can be about 0.2 to 20 wt %, or about 0.1, 0.2, 0.3, 0.4, 0.5, 1, 2, 3, 4, 5, 6, 7, 8, 9, 10, 15, or 20 wt %.

Examples of suitable crosslinking agents are boron-containing compounds and polyvalent metals such as titanium or zirconium. Boron-containing compounds include boric acid, diborates, tetraborates, pentaborates, polymeric compounds such as Polybor®, polymeric compounds of boric acid, and alkali borates, for example. These agents can be used to produce borate crosslinks between poly alpha-1,3-glucan ether molecules. Titanium crosslinks may be produced using titanium IV-containing compounds (e.g., titanium ammonium lactate, titanium triethanolamine, titanium acetylacetonate, polyhydroxy complexes of titanium) as crosslinking agents. Zirconium crosslinks can be produced using zirconium IV-containing compounds (e.g., zirconium lactate, zirconium carbonate, zirconium acetylacetonate, zirconium triethanolamine, zirconium diisopropylamine lactate, polyhydroxy complexes of zirconium) as crosslinking agents. Other examples of crosslinking agents useful herein are described in U.S. Pat. Nos. 4,462,917, 4,464,270, 4,477, 360 and 4,799,550, which are all incorporated herein by reference.

The pH of the solution or mixture containing both a crosslinking agent(s) and a poly alpha-1,3-glucan ether compound(s) can be adjusted to be alkali (e.g., pH of 8, 8.5, 9, 9.5, or 10). Modification of pH can be done by any means known in the art, such as with a concentrated aqueous solution of an alkali hydroxide such as sodium hydroxide. Dissolving a crosslinking agent in a solution or mixture containing one or more poly alpha-1,3-glucan ether compounds at an alkali pH results in crosslinking of the poly alpha-1,3-glucan ether compound(s).

EXAMPLES

The disclosed invention is further defined in the following Examples. It should be understood that these Examples, while indicating certain preferred aspects of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

Preparation of Poly Alpha-1,3-Glucan

Poly alpha-1,3-glucan was prepared using a gtfJ enzyme preparation as described in U.S. Patent Appl. Publ. No. 2013/0244288, which is incorporated herein by reference in its entirety.

$^1$H Nuclear Magnetic Resonance (NMR) Method for Determining Molar Substitution of Poly Alpha-1,3-Glucan Ether Derivatives Approximately 30 mg of the poly alpha-1,3-glucan ether derivative was weighed into a vial on an analytical balance. The vial was removed from the balance and 1.0 mL of deuterium oxide was added to the vial. A magnetic stir bar was added to the vial and the mixture was stirred to suspend the solid. Deuterated sulfuric acid (50% v/v in $D_2O$), 1.0 mL, was then added to the vial and the mixture was heated at 90° C. for 1 hour in order to depolymerize and solubilize the polymer. The solution was allowed to cool to room temperature and then a 0.8 mL portion of the solution was transferred into a 5-mm NMR tube using a glass pipet. A quantitative $^1$H NMR spectrum was acquired using an Agilent VNMRS 400 MHz NMR spectrometer equipped with a 5-mm Autoswitchable Quad probe. The spectrum was acquired at a spectral frequency of 399.945 MHz, using a spectral window of 6410.3 Hz, an acquisition time of 3.744 seconds, an inter-pulse delay of 10 seconds and 64 pulses. The time domain data were transformed using exponential multiplication of 0.50 Hz.

Determination of Degree of Polymerization

Degree of polymerization (DP) was determined by size exclusion chromatography (SEC). For SEC analysis, dry poly alpha-1,3-glucan ether derivative was dissolved in phosphate-buffered saline (PBS) (0.02-0.2 mg/mL). The chromatographic system used was an Alliance™ 2695 liquid chromatograph from Waters Corporation (Milford, Mass.) coupled with three on-line detectors: a differential refractometer 410 from Waters, a multi-angle light-scattering photometer Heleos™ 8+ from Wyatt Technologies (Santa Barbara, Calif.), and a differential capillary viscometer ViscoStar™ from Wyatt Technologies. The columns used for SEC were two Tosoh Haas Bioscience TSK GMPW$_{XL}$ g3K and g4K G3000PW and G4000PW polymeric columns for aqueous polymers. The mobile phase was PBS. The chromatographic conditions used were 30° C. at column and detector compartments, 30° C. at sample and injector compartments, a flow rate of 0.5 mL/min, and injection volume of 100 μL. The software packages used for data reduction were Astra version 6 from Wyatt (triple detection method with column calibration).

Homogenization

Homogenization was performed using an IKA ULTRA TURRAX T25 Digital Homogenizer (IKA, Wilmington, N.C.).

Example 1

Preparation of Quaternary Ammonium Poly Alpha-1,3-Glucan

This Example describes producing a quaternary ammonium poly alpha-1,3-glucan ether derivative. Specifically, trimethylammonium hydroxypropyl poly alpha-1,3-glucan was produced.

10 g of poly alpha-1,3-glucan ($M_w$ [weight-average molecular weight]=168,000) was added to 100 mL of isopropanol in a 500-mL capacity round bottom flask fitted with a thermocouple for temperature monitoring and a condenser connected to a recirculating bath, and a magnetic stir bar. 30 mL of sodium hydroxide (17.5% solution) was added dropwise to this preparation, which was then heated to 25° C. on a hotplate. The preparation was stirred for 1 hour before the temperature was increased to 55° C. 3-chloro-2-hydroxypropyl-trimethylammonium chloride (31.25 g) was then added to provide a reaction, which was held at 55° C. for 1.5 hours before being neutralized with 90% acetic acid. The solid thus formed (trimethylammonium hydroxypropyl poly alpha-1,3-glucan) was collected by vacuum filtration and washed with ethanol (95%) four times, dried under vacuum at 20-25° C., and analyzed by NMR and SEC to determine molecular weight and DoS.

Additional samples of trimethylammonium hydroxypropyl poly alpha-1,3-glucan were synthesized following the above process, but with certain process variations. Specifically, poly alpha-1,3-glucan samples with various $M_w$'s were used as starting material, and different amounts of etherification agent (3-chloro-2-hydroxypropyl-trimethylammonium chloride) were used. Also, reaction time (beginning from addition of etherification agent and ending at neutralization) was varied. Table 1 lists these various process variations and the resulting DoS measurements of the quaternary ammonium glucan ether products.

TABLE 1

DoS of Quaternary Ammonium Hydroxypropyl Poly Alpha-1,3-Glucan Prepared from Poly Alpha-1,3-Glucan

| Sample Designation | $M_w$ of poly alpha-1,3-glucan starting material | Etherification Agent Amount | Reaction Time (hours)[a] | DoS |
|---|---|---|---|---|
| 1A | 99231 | 31.25 g | 3 | 1.26 |
| 1B-1 | 99231 | 31.25 g | 1 | 0.59 |
| 1B-2 | | | 2 | 1.05 |
| 1B-3 | | | 4 | 1.29 |
| 1C-1 | 99231 | 9 g | 1 | 0.39 |
| 1C-2 | | | 2 | 0.35 |
| 1C-3 | | | 4 | 0.31 |
| 1D | 168000 | 15 g | 2.5 | 0.43 |
| 1E-1 | 189558 | 18 g | 1 | 0.34 |
| 1E-2 | | | 2 | 0.37 |
| 1E-3 | | | 4 | 0.45 |
| 1F | 247182 | 31.25 g | 4 | 0.17 |
| 1G | 163200 | 31.25 g | 3 | 0.52 |
| 1F | 34083 | 31.25 g | 2.5 | 1.19 |

[a]Reaction time was measured from the time etherification agent was added to the time of reaction neutralization.

Thus, the quaternary ammonium glucan ether derivative, trimethylammonium hydroxypropyl poly alpha-1,3-glucan, was prepared and isolated.

Example 2

Effect of Shear Rate on Viscosity of Quaternary Ammonium Poly Alpha-1,3-Glucan

This Example describes the effect of shear rate on the viscosity of trimethylammonium hydroxypropyl poly alpha-1,3-glucan. It is shown that this glucan ether derivative exhibits shear thinning behavior. Thus, addition of trimethylammonium hydroxypropyl poly alpha-1,3-glucan to a liquid can modify the rheological behavior of the liquid.

Various samples of trimethylammonium hydroxypropyl poly alpha-1,3-glucan were prepared as described in Example 1. To prepare a 2 wt % solution of each sample, 1 g of sample was added to 49 g of DI water. Each preparation was then homogenized for 12-15 seconds at 20,000 rpm to dissolve the trimethylammonium hydroxypropyl poly alpha-1,3-glucan sample in the water.

To determine the viscosity of each 2 wt % quaternary ammonium glucan solution at various shear rates, each solution was subjected to various shear rates using a Brookfield DV III+ Rheometer equipped with a recirculating bath to control temperature (20° C.) and a ULA (ultra low adapter) spindle and adapter set. The shear rate was increased using a gradient program which increased from 10-250 rpm and the shear rate was increased by 4.9 1/s every 20 seconds for the ULA spindle and adapter. The results of the experiment are listed in Table 2.

TABLE 2

Viscosity of Quaternary Ammonium Hydroxypropyl Poly Alpha-1,3-Glucan Solutions at Various Shear Rates

| Sample[a] | Viscosity (cPs) @ 66.18 rpm | Viscosity (cPs) @ 102.9 rpm | Viscosity (cPs) @ 183.8 rpm | Viscosity (cPs) @ 250 rpm |
|---|---|---|---|---|
| 1A | 26.26 | 24.95 | 23.42 | 22.6 |
| 1B-1 | 98.87 | 83.22 | 70.27 | 64.43 |
| 1B-2 | 43.76 | 41.53 | 38.24 | 36.57 |
| 1B-3 | 21.53 | 20.08 | 19.16 | 18.72 |

TABLE 2-continued

Viscosity of Quaternary Ammonium Hydroxypropyl Poly Alpha-1,3-Glucan Solutions at Various Shear Rates

| Sample[a] | Viscosity (cPs) @ 66.18 rpm | Viscosity (cPs) @ 102.9 rpm | Viscosity (cPs) @ 183.8 rpm | Viscosity (cPs) @ 250 rpm |
|---|---|---|---|---|
| 1C-1 | 225.81 | 158.76 | 102.02 | 85.6 |
| 1C-2 | 1246.67 | 810.93 | 436.29 | 334.8 |
| 1C-3 | 1601.44 | 992.24 | 563.95 | 421.2 |
| 1E-1 | 739.62 | 493.41 | 269.67 | 224 |

[a]Each sample is described in Table 1.

The results summarized in Table 2 indicate that the viscosity of each of the quaternary ammonium poly alpha-1,3-glucan solutions is reduced as the shear rate is increased. This observation means that these solutions demonstrate shear thinning behavior.

Thus, trimethylammonium hydroxypropyl poly alpha-1,3-glucan when dissolved in an aqueous solution not only modifies the viscosity of the solution, but also the rheological properties of the solution. This quaternary ammonium glucan can therefore be added to an aqueous liquid to modify its rheological profile.

Example 3

Creating Calibration Curve for Direct Red 80 Dye Using UV Absorption

This example discloses creating a calibration curve useful for determining the relative level of adsorption of poly alpha-1,3-glucan ether derivatives onto fabric surfaces.

Solutions of known concentration (ppm) were made using Direct Red 80 dye. The absorbance of these solutions was measured using a LAMOTTE SMART2 Colorimeter at either 520 or 620 nm. The absorption information was plotted in order that it could be used to determine dye concentration of solutions which were exposed to fabric samples. The concentration and absorbance of each calibration curve are provided in Table 3.

TABLE 3

Direct Red 80 Dye Calibration Curve Data

| Dye Concentration (ppm) | Average Absorbance @520 nm |
|---|---|
| 25 | 0.823333333 |
| 22.5 | 0.796666667 |
| 20 | 0.666666667 |
| 15 | 0.51 |
| 10 | 0.37 |
| 5 | 0.2 |

Thus, a calibration curve was prepared that is useful for determining the relative level of adsorption of poly alpha-1,3-glucan ether derivatives onto fabric surfaces. This calibration curve was utilized in Example 4.

Example 4

Adsorption of Quaternary Ammonium Poly Alpha-1,3-Glucan Ether on Various Fabrics This example discloses testing the degree of adsorption of a quaternary ammonium poly alpha-1,3-glucan (trimethylammonium hydroxypropyl poly alpha-1,3-glucan) on different types of fabrics.

A 0.07 wt % solution of trimethylammonium hydroxypropyl poly alpha-1,3-glucan (Sample 1F, Table 1) was made by dissolving 0.105 g of the polymer in 149.89 g of deionized water. This solution was divided into several aliquots with different concentrations of polymer and other components (Table 4). Such other components were acid (dilute hydrochloric acid) or base (sodium hydroxide) to modify pH, or NaCl salt.

TABLE 4

Quaternary Ammonium Poly Alpha-1,3-Glucan Solutions Used in Fabric Adsorption Studies

| Amount of NaCl (g) | Amount of Solution (g) | Polymer Concentration (wt %) | Amount of Acid (g) | Amount of Base (g) | Final pH |
|---|---|---|---|---|---|
| 0 | 15 | 0.07 | n/a | n/a | ~7 |
| 0.15 | 14.85 | 0.0693 | n/a | n/a | ~7 |
| 0.3 | 14.7 | 0.0686 | n/a | n/a | ~7 |
| 0.45 | 14.55 | 0.0679 | n/a | n/a | ~7 |
| 0 | 9.7713 | 0.0683 | 0.2783 | n/a | 2.92 |
| 0 | 9.7724 | 0.0684 | 0.2369 | n/a | 4.96 |
| 0 | 10.0311 | 0.0702 | n/a | 0.0319 | 9.04 |
| 0 | 9.9057 | 0.0693 | n/a | 0.1059 | 11.05 |

Four different fabric types (cretonne, polyester, 65:35 polyester/cretonne, bleached cotton) were cut into 0.17 g pieces. Each piece was placed in a 2-mL well in a 48-well cell culture plate. Each fabric sample was exposed to 1 mL of each of the above solutions (Table 4) for a total of 36 samples (a control solution with no polymer was included for each fabric test). The fabric samples were allowed to sit for at least 30 minutes in the polymer solutions. The fabric samples were removed from the polymer solutions and rinsed in DI water for at least one minute to remove any unbound polymer. The fabric samples were then dried at 60° C. for at least 30 minutes until constant dryness was achieved. The fabric samples were weighed after drying and individually placed in 2-mL wells in a clean 48-well cell culture plate. The fabric samples were then exposed to 1 mL of a 250 ppm Direct Red 80 dye solution. The samples were left in the dye solution for at least 15 minutes. Each fabric sample was removed from the dye solution, afterwhich the dye solution was diluted 10×.

The absorbance of the diluted solutions was measured compared to a control sample. A relative measure of glucan polymer adsorbed to the fabric was calculated based on the calibration curve created in Example 3 for Direct Red 80 dye. Specifically, the difference in UV absorbance for the fabric samples exposed to polymer compared to the controls (fabric not exposed to polymer) represents a relative measure of polymer adsorbed to the fabric. This difference in UV absorbance could also be expressed as the amount of dye bound to the fabric (over the amount of dye bound to control), which was calculated using the calibration curve (i.e., UV absorbance was converted to ppm dye). Table 5 provides "dye (ppm)"; a positive value represents the dye amount that was in excess to the dye amount bound to the control fabric, whereas a negative value represents the dye amount that was less than the dye amount bound to the control fabric. A positive value reflects that the glucan ether compound adsorbed to the fabric surface.

TABLE 5

Relative Amount of Quaternary Ammonium Poly
Alpha-1,3-Glucan Bound to Different Fabrics Under
Different Conditions

| Cretonne | | Polyester | | 65:35 Polyester/ Cretonne | | Bleached Cotton | |
|---|---|---|---|---|---|---|---|
| Salt Conc. | dye (ppm)[a] | Salt Conc. | dye (ppm)[a] | Salt Conc. | dye (ppm)[a] | Salt Conc. | dye (ppm)[a] |
| 0[b] | +4.56 | 0[b] | +0.48 | 0[b] | +1.27 | 0[b] | +3.13 |
| 1%[b] | +1.97 | 1%[b] | +0.46 | 1%[b] | +0.58 | 1%[b] | +3.78 |
| 2%[b] | −0.52 | 2%[b] | +0.0003 | 2%[b] | +0.16 | 2%[b] | +4.11 |
| 3%[b] | 0 | 3%[b] | +0.10 | 3%[b] | +0.07 | 3%[b] | −0.13 |
| pH[c] | | pH[c] | | pH[c] | | pH[c] | |
| 3 | +2.06 | 3 | −0.29 | 3 | −0.26 | 3 | +2.97 |
| 5 | +3.13 | 5 | +0.13 | 5 | −0.33 | 5 | +2.87 |
| 9 | +2.05 | 9 | −0.003 | 9 | +0.07 | 9 | +4.69 |
| 11 | +2.02 | 11 | −0.59 | 11 | +0.12 | 11 | +2.03 |

[a]Amount of dye bound to fabric. A positive value represents the dye amount that was in excess to the dye amount bound to control. A positive dye amount in turn represents the relative amount of glucan ether adsorbed to the fabric.
[b]The pH of binding conditions was about 7 (refer to Table 4).
[c]Binding conditions did not include salt (refer to Table 4).

The data in Table 5 indicate that quaternary ammonium glucan polymer can adsorb to various types of fabric under different salt and pH conditions. This adsorption occurs even though the fabrics were rinsed after exposure to the polymer. It is notable that the glucan ether was able to adsorb to polyester and the polyester/cretonne blend, in addition to adsorbing to cotton.

Thus, a poly alpha-1,3-glucan ether derivative in an aqueous composition can adsorb to fabric.

What is claimed is:

1. A composition comprising a poly alpha-1,3-glucan ether compound represented by the structure:

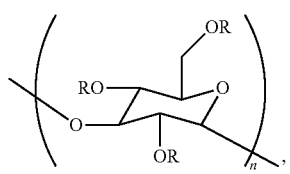

wherein
(i) n is at least 6,
(ii) each R is independently an H or a positively charged organic group,
(iii) the compound has a degree of substitution up to about 3.0, and
(iv) at least 80% of the glycosidic linkages of the poly alpha-1,3-glucan ether compound are alpha-1,3 glycosidic linkages,
and wherein at least one positivity charged organic group is a quaternary ammonium hydroxpropyl group.

2. The composition of claim 1, wherein the quaternary ammonium hydroxypropyl group comprises trialkylammonium.

3. The composition of claim 2, wherein the trialkylammonium is trimethylammonium.

4. The composition of claim 1, wherein the poly alpha-1,3-glucan ether compound has one or more of the same positively charged organic group.

5. The composition of claim 1, wherein the poly alpha-1,3-glucan ether compound has two or more different positively charged organic groups.

6. The composition of claim 1, wherein the poly alpha-1,3-glucan ether compound further comprises at least one nonionic organic group.

7. The composition of claim 1, wherein at least 90% of the glycosidic linkages of the poly alpha-1,3-glucan ether compound are alpha-1,3 glycosidic linkages.

8. The composition of claim 7, wherein at least 95% of the glycosidic linkages of the poly alpha-1,3-glucan ether compound are alpha-1,3 glycosidic linkages.

9. The composition of claim 1, wherein the composition is a personal care product, household product, industrial product, pharmaceutical product, or food product.

10. The composition of claim 1, wherein the composition is a fabric care product.

11. The composition of claim 1, wherein the composition comprises at least one surfactant.

12. The composition of claim 1, wherein the composition comprises at least one enzyme.

13. The composition of claim 1, wherein the composition is an aqueous composition.

14. The composition of claim 1, wherein the composition comprises fiber and said poly alpha-1,3-glucan ether compound.

15. The composition of claim 14, wherein said poly alpha-1,3-glucan ether compound is on the surface of the composition.

16. The composition of claim 14, wherein the fiber is a natural fiber.

17. The composition of claim 16, wherein natural fiber comprises cellulosic fiber.

18. The composition of claim 14, wherein the fiber is a synthetic fiber.

19. The composition of claim 18, wherein the synthetic fiber comprises polyester.

20. The composition of claim 14, wherein the fiber is a semi-synthetic fiber, optionally wherein the semi-synthetic fiber comprises rayon.

21. The composition of claim 14, wherein the composition is fabric.

22. The composition of claim 14, wherein the composition is non-woven fabric, padding, or foam.

23. The composition of claim 14, wherein the composition is paper.

24. A method of producing a poly alpha-1,3-glucan ether compound, the method comprising:
(a) contacting poly alpha-1,3-glucan in a reaction under alkaline conditions with at least one etherification agent comprising a positively charged organic group, wherein at least one positively charged organic group is etherified to the poly alpha-1,3-glucan thereby producing a poly alpha-1,3-glucan ether compound represented by the structure:

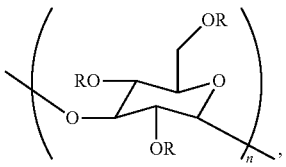

wherein
(i) n is at least 6,
(ii) each R is independently an H or the positively charged organic group, (iii) the compound has a degree of substitution up to about 3.0, and
(iv) at least 80% of the glycosidic linkages of the poly alpha-1,3-glucan ether compound are alpha-1,3 glycosidic linkages, and
wherein the etherification agent is 3-chloro-2-hydroxypropyl trimethyl ammonium chloride; and
(b) optionally, isolating the poly alpha-1,3-glucan ether compound produced in step (a).

25. A method for increasing the viscosity of an aqueous composition, the method comprising:
contacting a poly alpha-1,3-glucan ether compound with the aqueous composition, wherein the viscosity of the aqueous composition is increased by said compound, wherein said compound is represented by the structure:

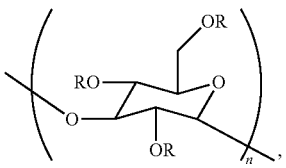

wherein
(i) n is at least 6,
(ii) each R is independently an H or the positively charged organic group,
(iii) the compound has a degree of substitution up to about 3.0, and
(iv) at least 80% of the glycosidic linkages of the poly alpha-1,3-glucan ether compound are alpha-1,3 glycosidic linkages,
and wherein at least one positively charged organic group is a quaternary ammonium hydroxypropyl group.

26. A method of treating a material, said method comprising:
contacting a material with an aqueous composition comprising a poly alpha-1,3-glucan ether compound represented by the structure:

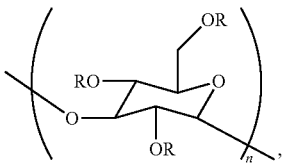

wherein
(i) n is at least 6,
(ii) each R is independently an H or the positively charged organic group,
(iii) the compound has a degree of substitution up to about 3.0, and
(iv) at least 80% of the glycosidic linkages of the poly alpha-1,3-glucan ether compound are alpha-1,3 glycosidic linkages,
and wherein at least one positivity charged organic group is a quaternary ammonium hydroxypropyl group.

27. The method of claim 26, wherein the material comprises fabric.

28. A composition comprising a poly alpha-1,3-glucan ether compound represented by the structure:

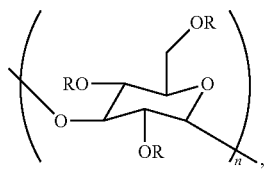

wherein
(i) n is at least 6,
(ii) each R is independently an H or a positively charged organic group,
(iii) the compound has a degree of substitution up to about 3.0, and
(iv) at least 80% of the glycosidic linkages of the poly alpha-1,3-glucan ether compound are alpha-1,3 glycosidic linkages,
and wherein the poly alpha-1,3-glucan ether compound has two or more different positively charged organic groups.

29. A composition comprising at least one surfactant and a poly alpha-1,3-glucan ether compound represented by the structure:

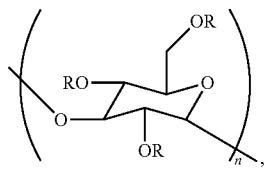

wherein
(i) n is at least 6,
(ii) each R is independently an H or a positively charged organic group,
(iii) the compound has a degree of substitution up to about 3.0, and
(iv) at least 80% of the glycosidic linkages of the poly alpha-1,3-glucan ether compound are alpha-1,3 glycosidic linkages.

30. The composition of claim 29, wherein at least one positively charged organic group comprises a substituted ammonium group.

31. The composition of claim 30, wherein the positively charged organic group comprises trialkylammonium.

32. The composition of claim 31, wherein the trialkylammonium is trimethylammonium.

33. The composition of claim 29, wherein at least one positively charged organic group comprises an alkyl group or hydroxy alkyl group.

34. The composition of claim 33, wherein at least one positively charged organic group is a quaternary ammonium hydroxypropyl group.

35. The composition of claim 29, wherein the poly alpha-1,3-glucan ether compound further comprises at least one nonionic organic group.

36. The composition of claim 29, wherein at least 90% of the glycosidic linkages of the poly alpha-1,3-glucan ether compound are alpha-1,3 glycosidic linkages.

37. The composition of claim 36, wherein at least 95% of the glycosidic linkages of the poly alpha-1,3-glucan ether compound are alpha-1,3 glycosidic linkages.

38. The composition of claim 29, wherein the composition is a personal care product, household product, industrial product, pharmaceutical product, or food product.

39. The composition of claim 29, wherein the composition is a fabric care product.

40. The composition of claim 29, wherein the composition comprises at least one enzyme.

41. A composition comprising at least one enzyme and a poly alpha-1,3-glucan ether compound represented by the structure:

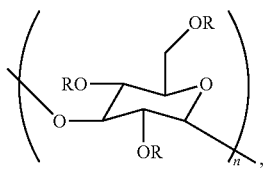

wherein
(i) n is at least 6,
(ii) each R is independently an H or a positively charged organic group,
(iii) the compound has a degree of substitution up to about 3.0, and
(iv) at least 80% of the glycosidic linkages of the poly alpha-1,3-glucan ether compound are alpha-1,3 glycosidic linkages.

42. The composition of claim 41, wherein at least one positively charged organic group comprises a substituted ammonium group.

43. The composition of claim 42, wherein the positively charged organic group comprises trialkylammonium.

44. The composition of claim 43, wherein the trialkylammonium is trimethylammonium.

45. The composition of claim 41, wherein at least one positively charged organic group comprises an alkyl group or hydroxy alkyl group.

46. The composition of claim 45, wherein at least one positively charged organic group is a quaternary ammonium hydroxypropyl group.

47. The composition of claim 41, wherein at least 90% of the glycosidic linkages of the poly alpha-1,3-glucan ether compound are alpha-1,3 glycosidic linkages.

48. The composition of claim 41, wherein the composition is a personal care product, household product, industrial product, pharmaceutical product, or food product.

49. The composition of claim 41, wherein the composition is a fabric care product.

50. The composition of claim 41, wherein the composition comprises at least one surfactant.

51. A composition comprising fiber and a poly alpha-1,3-glucan ether compound represented by the structure:

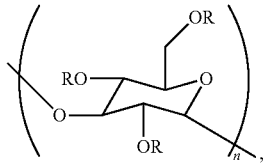

wherein
(i) n is at least 6,
(ii) each R is independently an H or a positively charged organic group,
(iii) the compound has a degree of substitution up to about 3.0, and
(iv) at least 80% of the glycosidic linkages of the poly alpha-1,3-glucan ether compound are alpha-1,3 glycosidic linkages.

52. The composition of claim 51, wherein at least one positively charged organic group comprises a substituted ammonium group.

53. The composition of claim 52, wherein the positively charged organic group comprises trialkylammonium.

54. The composition of claim 53, wherein the trialkylammonium is trimethylammonium.

55. The composition of claim 51, wherein at least one positively charged organic group comprises an alkyl group or hydroxy alkyl group.

56. The composition of claim 55, wherein at least one positively charged organic group is a quaternary ammonium hydroxypropyl group.

57. The composition of claim 51, wherein at least 90% of the glycosidic linkages of the poly alpha-1,3-glucan ether compound are alpha-1,3 glycosidic linkages.

58. The composition of claim 51, wherein said poly alpha-1,3-glucan ether compound is on the surface of the composition.

59. The composition of claim 51, wherein the fiber is a natural fiber.

60. The composition of claim 59, wherein natural fiber comprises cellulosic fiber.

61. The composition of claim 51, wherein the fiber is a synthetic fiber.

62. The composition of claim 61, wherein the synthetic fiber comprises polyester.

63. The composition of claim 51, wherein the fiber is a semi-synthetic fiber, optionally wherein the semi-synthetic fiber comprises rayon.

64. The composition of claim 51, wherein the composition is fabric.

65. The composition of claim 51, wherein the composition is non-woven fabric, padding, or foam.

66. The composition of claim 51, wherein the composition is paper.

67. A method of treating a material that comprises fabric, said method comprising:
contacting said material with an aqueous composition comprising a poly alpha-1,3-glucan ether compound represented by the structure:

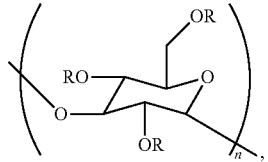

wherein
(i) n is at least 6,
(ii) each R is independently an H or the positively charged organic group,
(iii) the compound has a degree of substitution up to about 3.0, and
(iv) at least 80% of the glycosidic linkages of the poly alpha-1,3-glucan ether compound are alpha-1,3 glycosidic linkages.

* * * * *